United States Patent [19]

Pitteloud

[11] Patent Number: 5,777,113
[45] Date of Patent: Jul. 7, 1998

[54] HALS PHOSPHORINANES AS STABILISERS

[75] Inventor: Rita Pitteloud, Praroman, Switzerland

[73] Assignee: Ciba Specialty Chemicals Corporation, Tarrytown, N.Y.

[21] Appl. No.: 540,513

[22] Filed: Oct. 10, 1995

[51] Int. Cl.[6] .................................................. C07D 401/14
[52] U.S. Cl. .......................... 544/198; 544/113; 544/114; 546/15; 546/22; 546/187; 546/208
[58] Field of Search ........................... 544/113, 114, 544/198, 209; 546/15, 22, 187, 208

[56] References Cited

U.S. PATENT DOCUMENTS

| | | | |
|---|---|---|---|
| 3,904,581 | 9/1975 | Murayama et al. | 260/45.8 N |
| 3,974,127 | 8/1976 | Tanikella et al. | 260/75 N |
| 4,210,576 | 7/1980 | DiBattista et al. | 260/45.8 NE |
| 4,279,804 | 7/1981 | Cantatore et al. | 260/45.8 N |
| 4,293,466 | 10/1981 | DiBattista et al. | 260/45.8 N |
| 4,396,769 | 8/1983 | Ferreira et al. | 546/188 |
| 4,569,997 | 2/1986 | Karrer | 546/19 |
| 4,731,448 | 3/1988 | Issler et al. | 546/248 |
| 4,798,836 | 1/1989 | Minagawa et al. | 524/89 |
| 4,883,870 | 11/1989 | Cantatore et al. | 540/598 |
| 5,198,546 | 3/1993 | Borzatta et al. | 544/198 |
| 5,239,076 | 8/1993 | Meier et al. | 546/187 |
| 5,405,891 | 4/1995 | Pitteloud | 524/102 |

FOREIGN PATENT DOCUMENTS

| | | |
|---|---|---|
| 0042622 | 12/1981 | European Pat. Off. . |
| 0047967 | 3/1982 | European Pat. Off. . |
| 0149259 | 7/1985 | European Pat. Off. . |
| 0302020 | 2/1989 | European Pat. Off. . |
| 0314472 | 5/1989 | European Pat. Off. . |
| 0336895 | 10/1989 | European Pat. Off. . |
| 0356688 | 3/1990 | European Pat. Off. . |
| 0601973 | 6/1994 | European Pat. Off. . |
| 2380290 | 9/1978 | France . |
| 2233121 | 1/1973 | Germany . |
| 2353538 | 8/1974 | Germany . |
| 4306747 | 9/1993 | Germany . |
| 57-21368 | 2/1982 | Japan . |
| 2010275 | 6/1979 | United Kingdom . |
| 2247241 | 2/1992 | United Kingdom . |

OTHER PUBLICATIONS

R. Gachter/H. Muller (Ed.), Plastics Additives Handbook, 3rd. Ed., p. 47, Hanser, Munchen (1990).
T. Konig et al., J. Prakt Chem., 334, pp. 333–349, (1992).
Derwent Abstract 93–296322/38 of DE4306747, 1993.
Houben–Weyl, Methoden der Organischen Chemie E1, pp. 373–376 (1982).
J.H. R.O. Day et al, Inorg. Chem., vol. 31, pp. 1279–1285 (1992).
Von B. Costisella et al., Journal für Praktische Chemie, Band vol. 314 (3–4), pp. 532–542 (1972).
Beilstein E II, vol. 22, p. 321 (1953).
Derwent Abstract 73:04455u/04 of DE2233121 1973.
Derwent Abstract 74–34584V/19 of DE2353538 1974.
Derwent Abstract 77–22939Y/13 of FR2380290, 1977.

*Primary Examiner*—Yogendra N. Gupta
*Attorney, Agent, or Firm*—Luther A. R. Hall; David R. Crichton; Victoria M. Malia

[57] ABSTRACT

The invention relates to novel compounds of formula I

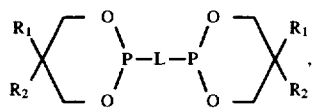

wherein the general symbols are as defined in claim 1, as stabilizers for organic materials against oxidative, thermal or light-induced degradation.

7 Claims, No Drawings

HALS PHOSPHORINANES AS STABILISERS

The present invention relates to novel HALS phosphorinanes, to compositions comprising an organic material, preferably a polymer, as well as said novel HALS phosphorinanes, and to the use thereof for stabilising organic materials against oxidative, thermal or light-induced degradation.

Organic phosphites and phosphonites are known in the art as co-stabilisers, secondary antioxidants and processing stabilisers, inter alia for polyolefins. Examples of such known phosphite stabilisers will be found in R. G achter/H. Müller (Ed.), Plastics Additives Handbook. 3rd Ed., p. 47, Hanser, Munich 1990, and in EP-A-356 688.

Hindered amines, including in particular compounds containing 2,2,6,6-tetramethylpiperidyl groups, preferably find utility as light stabilisers (hindered amine light stabilisers; HALS).

Phosphites and phosphonites containing HALS structural units are disclosed, inter alia, in T. König et al, J. prakt. Chem. 334, 333–349 (1992), in U.S. Pat. No. 5,239,076, GB-A-2 247 241, DE-A-4 306 747, FR-A-2 380 290, EP-A-0 042 622, EP-A-0 149 259 and U.S. Pat. No. 4,293, 466.

There is still a need to provide effective stabilisers for organic materials which are susceptible to oxidative, thermal and/or light-induced degradation.

It has now been found that a selected group of such HALS phosphites is particularly suitable for use as stabilisers for organic materials which are susceptible to oxidative, thermal or light-induced degradation. The suitability of said compounds as processing stabilisers for synthetic polymers is to be singled out for special mention.

Accordingly, the present invention relates to compounds of formula I

(I)

wherein L is a group of formula II or III $-O-R_3-O-$ (II)

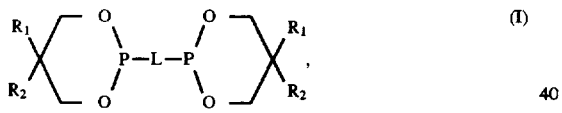
(III)

wherein $R_1$ and $R_2$ are each independently of the other hydrogen or $C_1$–$C_4$alkyl or, together with the linking carbon atom, are a 3,4-dehydrocyclohexylidene ring or 5-norbornenylidene ring.

$R_3$ is a group of formulae IV to XVI

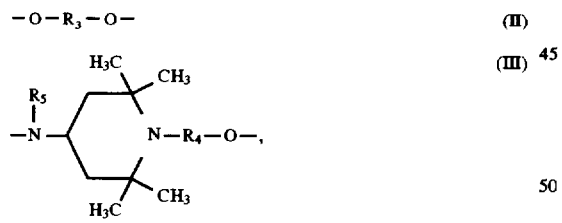
(IV)

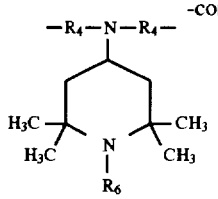
(V)

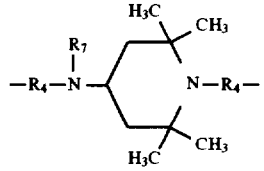
(VI)

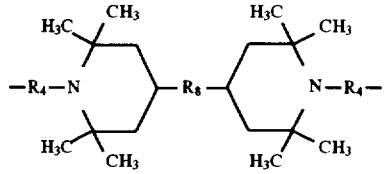
(VII)

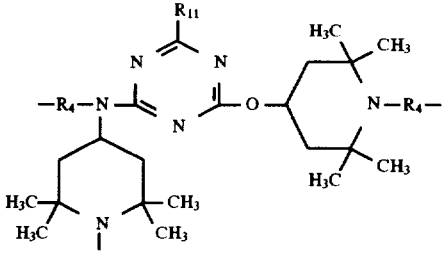
(XIII)

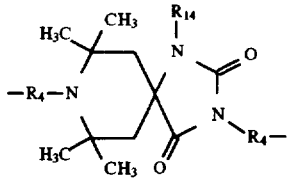
(XIV)

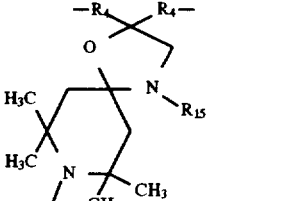
(XV)

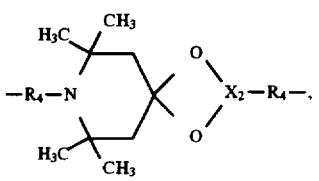
(XVI)

$R_4$ is $C_1$–$C_{18}$alkylene, $C_2$–$C_{18}$alkylene which is interrupted by oxygen, sulfur or

$C_4$–$C_8$alkenylene or phenylethylene, $R_5$ is $C_1$–$C_8$alkyl or a radical of formula XVII
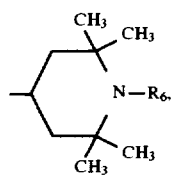
(XVII)
$R_6$ is hydrogen, $C_1$–$C_8$alkyl, $O^{108}$, OH, NO, —CH$_2$CN, $C_1$–$C_{18}$alkoxy, $C_5$–$C_{12}$cycloalkoxy, $C_3$–$C_6$alkenyl, $C_3$–$C_6$alkynyl, $C_1$–$C_8$acyl, $C_7$–$C_9$phenylalkyl which is unsubstituted or substituted at the phenyl ring by $C_1$–$C_4$alkyl;
$R_7$ is $C_1$–$C_8$alkyl or a radical of formula XVII
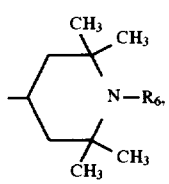
(XVII)
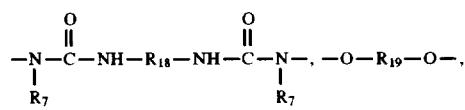
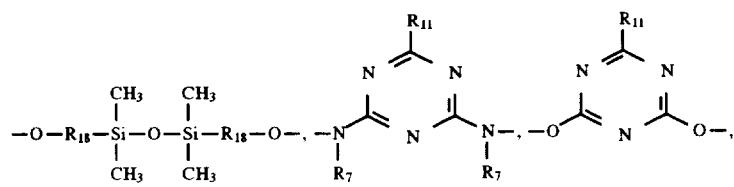
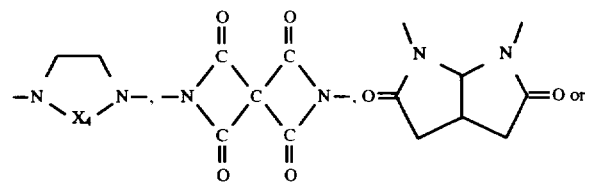
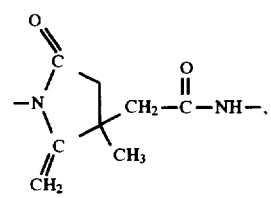
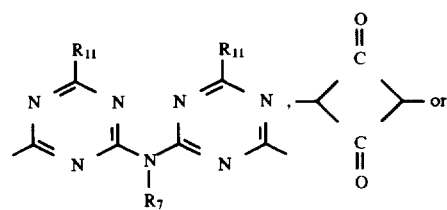

-continued

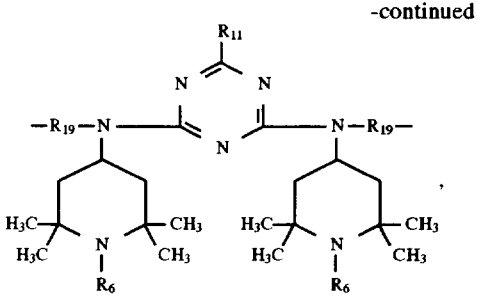

$R_{10}$ is $C_1$–$C_8$alkyl or a radical of formula XVII

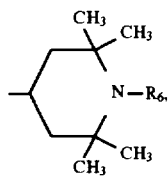

(XVII)

$R_{11}$ is —$OR_{21}$, —$NHR_{22}$,

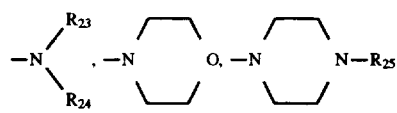

or —$SR_{21}$.

$R_{12}$ and $R_{13}$ are each independently of the other

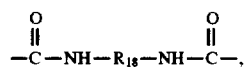

$C_1$–$C_{18}$alkylene, $C_2$–$C_{18}$alkylene which is interrupted by oxygen, sulfur or

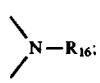

$C_2$–$C_{18}$alkenylene, $C_2$–$C_{18}$alkynylene, $C_2$–$C_{20}$alkylidene, $C_7$–$C_{20}$phenylalkylidene, $C_5$–$C_8$cycloalkylene, $C_7$–$C_8$bicycloalkylene; phenylene or naphthylene which are unsubstituted or substituted by $C_1$–$C_4$alkyl;

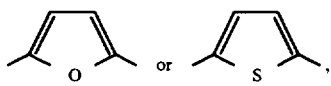

$R_{14}$ and $R_{15}$ are each independently of the other hydrogen or $C_1$–$C_8$alkyl.

$R_{16}$ is hydrogen or $C_1$–$C_8$alkyl.

$R_{17}$ is $C_1$–$C_8$alkyl.

$R_{18}$ is a direct bond, $C_1$–$C_{18}$alkylene, $C_2$–$C_{18}$alkylene which is interrupted by oxygen, sulfur or

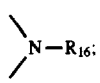

$C_2$–$C_{18}$alkenylene, $C_2$–$C_{20}$alkylidene, $C_7$–$C_{20}$phenylalkylidene, $C_5$–$C_{18}$cycloalkylene, $C_7$–$C_{18}$bicycloalkylene, phenylene or naphthylene which are unsubstituted or substituted by $C_1$–$C_4$alkyl;

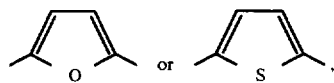

$R_{19}$ is $C_1$–$C_{18}$alkylene, $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, phenylene or naphthylene which are unsubstituted or substituted by $C_1$–$C_4$alkyl;

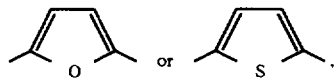

$R_{20}$ is $C_1$–$C_{25}$alkanoyl, benzoyl which is unsubstituted or substituted by $C_1$–$C_{12}$-alkyl; or

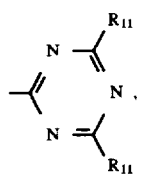

$R_{21}$ is $C_1$–$C_{25}$alkyl, $C_2$–$C_{25}$alkyl which is interrupted by oxygen, sulfur or

$C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; $C_7$–$C_9$phenylalkyl which is unsubstituted or substituted at the phenyl ring by $C_1$–$C_4$alkyl; phenyl which is unsubstituted or substituted by $C_1$–$C_4$alkyl;

$R_{22}$, $R_{23}$, $R_{24}$ and $R_{25}$ are each independently of one another hydrogen, $C_1$–$C_{18}$alkyl or a radical of formula XVII

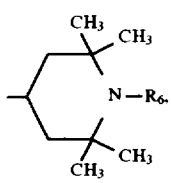

$R_{26}$ is $C_1$–$C_4$alkyl or hydroxymethyl,
$R_{27}$ is hydrogen or $C_1$–$C_8$alkyl,
$R_{28}$ is hydrogen, $C_1$–$C_8$alkyl or a radical of formula XVII

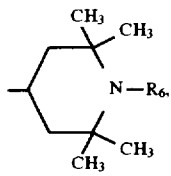

$R_{29}$ is hydrogen, $C_1$–$C_{20}$alkyl, $C_5$–$C_{12}$cycloalkyl, unsubstituted or $C_1$–$C_4$alkyl-substituted phenyl.
$X_1$ is a group of formula XVIII, XIX, XX or XXI

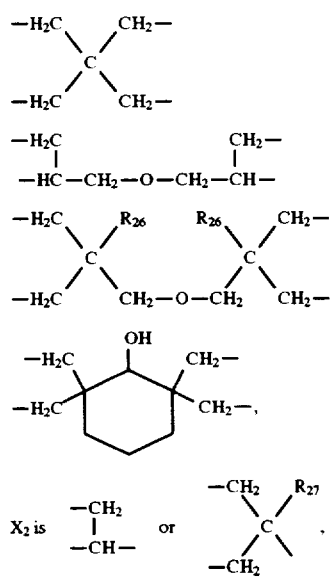

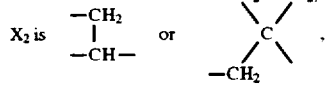

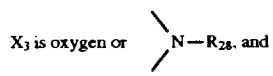

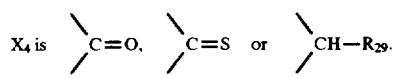

Alkyl of up to 25 carbon atoms is a branched or unbranched radical, typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of $R_{21}$ is $C_1$–$C_{18}$alkyl, preferably $C_1$–$C_{12}$alkyl, e.g. $C_1$–$C_8$alkyl. One of the preferred meanings of $R_5$, $R_6$, $R_7$, $R_{10}$, $R_{14}$, $R_{15}$, $R_{17}$, $R_{27}$ and $R_{28}$ is $C_1$–$C_6$alkyl, preferably $C_1$–$C_5$alkyl, e.g. $C_1$–$C_4$alkyl. A particularly preferred meaning of $R_{22}$, $R_{23}$, $R_{24}$ and $R_{25}$ is $C_1$–$C_{16}$alkyl, preferably $C_1$–$C_{14}$alkyl, e.g. $C_1$–$C_{12}$alkyl. A particularly preferred meaning of $R_{22}$, $R_{23}$, $R_{24}$ and $R_{25}$ is $C_1$–$C_{12}$alkyl, preferably $C_1$–$C_{10}$alkyl, e.g. $C_1$–$C_8$alkyl.

The 3,4-dehydrocyclohexylidene ring is

The 5-norbornenylidene ring is

Alkyl of 25 carbon atoms, which is interrupted by oxygen, sulfur or

may be interrupted once or more than once and is typically $CH_3$—O—$CH_2$—, $CH_3$—S—$CH_2$—, $CH_3$—NH—$CH_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—. A particularly preferred meaning of $R_{21}$ is $C_2$–$C_{18}$alkyl which is interrupted by oxygen, preferably $C_4$–$C_{18}$alkyl which is interrupted by oxygen, e.g. $C_4$–$C_{12}$alkyl which is interrupted by oxygen.

Alkenyl of 2 to 24 carbon atoms is a branched or unbranched radical, typically vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. A particularly preferred meaning of $R_{21}$ is alkenyl of 3 to 18, preferably 3 to 12, e.g. 3 to 10, carbon atoms. A particularly preferred meaning of $R_6$ is alkenyl of 3 to 6, preferably 3 to 5, e.g. 3 to 4, carbon atoms.

Unsubstituted or $C_1$–$C_4$alkyl-substituted $C_5$–$C_{15}$cycloalkyl, more particularly $C_5$–$C_{12}$cycloalkyl, which preferably contains 1 to 3, more particularly 1 or 2, branched or unbranched alkyl groups, is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclododecyl. Preference is given to $C_5$–$C_8$cycloalkyl and, in particular, cyclohexyl.

Unsubstituted or $C_1$–$C_4$alkyl-substituted $C_5$–$C_{15}$cycloalkenyl, which preferably contains 1 to 3, more particularly 1 or 2, branched or unbranched alkyl groups, is typically cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl, cyclooctenyl or cyclododecenyl. Preference is given to $C_5$–$C_{12}$cycloalkenyl and, in particular, $C_5$–$C_8$cycloalkenyl, e.g. cyclohexenyl.

$C_7$–$C_9$phenylalkyl which is unsubstituted or substituted at the phenyl radical by $C_1$–$C_4$alkyl and which preferably contains 1 to 3, more particularly 1 or 2, branched or unbranched alkyl groups is typically benzyl, α-methylbenzyl, (α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

$C_1$–$C_{18}$alkylene is a branched or unbranched radical, typically methylene, ethylene, propylene, tetramethylene, pentamethylene, hexamethylene, heptamethylene, octamethylene, decamethylene, dodecamethylene or octadecamethylene. A preferred meaning of $R_4$ is $C_1$–$C_{12}$alkylene, preferably $C_2$–$C_{10}$alkylene, e.g. $C_2$–$C_8$alkylene. Particularly preferred meanings of $R_4$ are ethylene and propylene. A preferred meaning of $_2$ and $R_{13}$ is $C_2$–$C_{14}$alkylene, preferably $_2$–$C_{12}$alkylene, e.g. $C_2$–$C_8$-akylene. A particularly preferred meaning of $R_{12}$ and $R_{13}$ is $C_4$–$C_8$alkylene. A preferred meaning of $R_{18}$ is $C_1$–$C_{14}$alkylene, preferably $C_1$–$C_{12}$alkylene, e.g. $C_1$–$C_8$alkylene. A preferred meaning of $R_{19}$ is $C_2$–$C_{14}$alkylene, preferably $C_2$–$C_{12}$alkylene, e.g. $C_2$–$C_8$-alkylene.

$C_{12}$–$C_{18}$alkylene which is interrupted by oxygen, sulfur or

can be interrupted once or more than once and is typically —CH$_2$—O—CH$_2$—, —CH$_2$—S—CH$_2$—, —CH$_2$—NH—CH$_2$—, —CH$_2$—N(CH$_3$)—CH$_2$—, —CH$_2$—O—CH$_2$CH$_2$—O—CH$_2$—, —CH$_2$—(O—CH$_2$CH$_2$—)$_2$O—CH$_2$—, —CH$_2$—(O—CH$_2$CH$_2$—)$_3$CH$_2$—, —CH$_2$—(O—CH$_2$CH$_2$—)$_4$O—CH$_2$— or —CH$_2$CH$_2$—S—CH$_2$CH$_2$—. A preferred meaning of $R_4$, $R_{12}$, $R_{13}$, $R_{18}$ and $R_{19}$ is $C_2$–$C_{18}$alkylene which is interrupted by oxygen, preferably $C_4$–$C_{18}$alkylene which is interrupted by oxygen, e.g. $C_4$–$C_{12}$alkylene which is interrupted by oxygen.

$R_4$ defined as $C_4$–$C_8$alkenylene is typically 2-buten-1,4-ylene.

Phenylethylene is —CH(C$_6$H$_5$)CH$_2$—.

$C_1$–$C_4$alkyl-substituted phenyl, which preferably contains 1 to 3, more particularly 1 or 2, alkyl groups, is typically o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Alkoxy of up to and including 18 carbon atoms is a branched or unbranched radical, typically methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. A preferred meaning of $R_6$ is alkoxy of 4 to 16, preferably 6 to 12, carbon atoms.

Cycloalkoxy of 5 to 12 carbon atoms is typically cyclopentoxy, cyclohexoxy, cycloheptoxy, cyclooctoxy, cyclodecyloxy or cyclododecyloxy. One of the preferred meanings of $R_4$ is $C_5$–$C_8$cycloalkoxy. Particular preference is given to cyclopentoxy and cyclohexoxy.

Alkynyl of 3 to 6 carbon atoms is a branched or unbranched radical, typically propynyl (propargyl) —CH$_2$—C≡CH), 2-butynyl or 3-butynyl.

Acyl of 1 to 8 carbon atoms is typically formyl, acetyl, propionyl, butyryl, pentanoyl, hexanoyl, heptanoyl, octanoyl, benzoyl, acryloyl or crotonyl. Preference is given to $C_1$–$C_8$-alkanoyl, $C_3$–$C_8$alkenoyl or benzoyl, more particularly acetyl.

Typically examples of $C_2$–$C_{18}$alkenylene are vinylene, methylvinylene, octenylethylene or dodecenylethylene. A preferred meaning of $R_{12}$, $R_{13}$, $R_{18}$ and $R_{19}$ is $C_4$–$C_{12}$alkenylene, preferably $C_4$–$C_8$alkenylene, e.g. 2-butenylene-1,4.

Illustrative examples of $C_2$–$C_{18}$alkynylene are —C≡C—, 2-propynylene (—C≡C—CH$_2$—), 2-butynylene (—CH$_2$—C≡C—CH$_2$—), 2-pentynylene, 2-hexynylene, 3-hexynylene, 3-heptynylene, 2-decynylene, 4-decynylene or 8-octadecynylene. A preferred meaning of $R_{12}$ and $R_{13}$ is $C_2$–$C_{12}$alkynylene, preferably $C_4$–$C_8$alkynylene, e.g. 2-butynylene.

Alkylidene of 2 to 20 carbon atoms is typically ethylidene, propyliden, butylidene, pentylidene, 4-methylpentylidene, heptylidene, nonylidene, tridecylidene, nonadecylidene, 1-methylethylidene, 1-ethylpropylidene or 1-ethylpentylidene. A preferred meaning of $R_{12}$, $R_{13}$, $R_{18}$ and $R_{19}$ is alkylidene of 2 to 12, preferably 2 to 8, e.g. 2 to 6, carbon atoms.

Phenylalkylidene of 7 to 20 carbon atoms is typically benzylidene, 2-phenylethylidene or 1-phenyl-2-hexylidene. One of the preferred meanings of $R_{12}$, $R_{13}$, $R_{18}$ and $R_{19}$ is phenylalkylidene of 7 to 15, preferably 7 to 12, e.g. 7 to 9, carbon atoms.

$C_5$–$C_8$Cycloalkylene is a saturated hydrocarbon group having two free valences and at least one ring unit and is typically cyclopentylene, cyclohexylene, cycloheptylene or cyclooctylene. Cyclohexylene is preferred.

$C_7$–$C_8$Bicycloalkylene is typically bicycloheptylene or bicyclooctylene.

Unsubstituted or $C_1$–$C_4$alkyl-substituted phenylene or naphthylene is typically 1,2-, 1,3-, 1,4-phenylene, 1,2-, 1,3-, 1,4-, 1,6-, 1,7-, 2,6- or 2,7-naphthylene. 1,4-phenylene is preferred.

Alkanoyl of up to 25 carbon atoms is a branched or unbranched radical, typically including formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. A preferred meaning of $R_{20}$ is $C_1$–$C_{18}$alkanoyl, preferably $C_1$–$C_{12}$alkanoyl, e.g. $C_1$–$C_8$alkanoyl. An especially preferred meaning of $R_{20}$ is $C_1$–$C_4$alkanoyl, more particularly acetyl.

$C_1$–$C_{12}$Alkyl-substituted benzoyl which preferably carries 1 to 3, more particularly 1 or 2, alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$alkyl, more particularly $C_1$–$C_4$alkyl.

Preferred compounds are those of formula I, wherein $R_4$ is $C_2$–$C_4$alkylene.

Also preferred are the compounds of formula I, wherein $R_4$ is $C_1$–$C_{12}$alkylene, $C_4$–$C_{18}$alkylene which is interrupted by oxygen or sulfur; or $C_4$–$C_8$alkenylene, $R_5$ is $C_1$–$C_8$alkyl, $R_6$ is hydrogen, $C_1$–$C_8$alkyl, $O^{108}$, $C_4$–$C_{18}$alkoxy, $C_5$–$C_8$cycloalkoxy, $C_3$–$C_6$alkenyl, $C_3$–$C_6$alkynyl, $C_1$–$C_6$acyl or benzyl, $R_7$ is $C_1$–$C_8$alkyl.

$R_8$ is 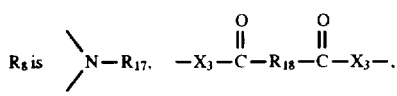

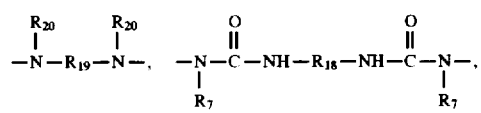

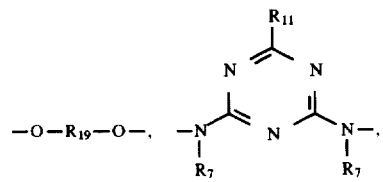

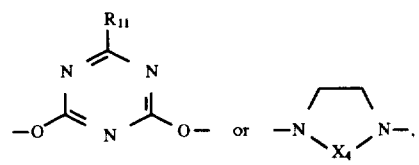

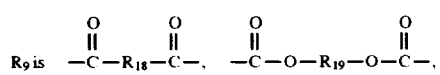

$R_9$ is 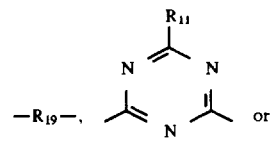

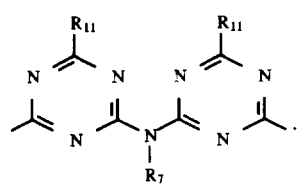

$R_{10}$ is $C_1$–$C_8$alkyl.

$R_{11}$ is —$OR_{21}$, —$NHR_{22}$, 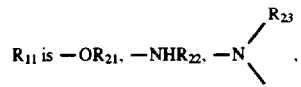

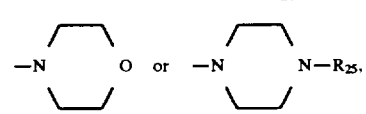

$R_{12}$ and $R_{13}$ are each independently of the other

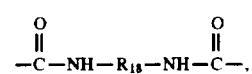

$C_1$–$C_{12}$alkylene, $C_4$–$C_{12}$alkylene which is interrupted by oxygen or sulfur; $C_2$–$C_{12}$alkenylene, $C_2$–$C_{12}$alkynylene, $C_2$–$C_{14}$alkylidene, $C_7$–$C_{16}$phenylalkylidene, $C_5$–$C_8$cycloalkylene, phenylene or naphthylene, $R_{14}$ and $R_{15}$ are each independently of the other hydrogen or $C_1$–$C_4$alkyl.

$R_{18}$ is a direct bond, $C_1$–$C_{18}$alkylene, $C_4$–$C_{12}$alkylene which is interrupted by oxygen or sulfur; $C_2$–$C_{12}$alkenylene, $C_2$–$C_{14}$alkylidene, $C_7$–$C_{16}$phenylalkylidene, $C_5$–$C_8$cycloalkylene, phenylene or naphthylene, $R_{19}$ is $C_1$–$C_{12}$alkylene, $C_2$–$C_{12}$alkylene which is interrupted by oxygen or sulfur; $C_2$–$C_{12}$alkenylene, $C_2$–$C_{14}$alkylidene, $C_7$–$C_{16}$phenylalkylidene, $C_5$–$C_8$cycloalkylene, phenylene or naphthylene, $R_{20}$ is $C_1$–$C_{18}$alkanoyl, benzoyl or

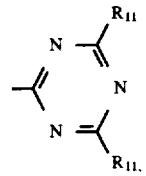

$R_{21}$ is $C_1$–$C_{18}$alkyl, $C_2$–$C_{18}$alkyl which is interrupted by oxygen or sulfur; $C_2$–$C_{18}$alkenyl, $C_5$–$C_{18}$cycloalkyl which is unsubstituted or substituted by $C_1$–$C_4$alkyl; $C_5$–$C_8$cycloalkenyl which is unsubstituted or substituted by $C_1$–$C_4$alkyl; $C_7$–$C_9$phenylalkyl, unsubstituted or $C_1$–$C_4$alkyl-substituted phenyl;

$R_{22}$, $R_{23}$, $R_{24}$ and $R_{25}$ are each independently of one another hydrogen or $C_1$–$C_{12}$alkyl.

$R_{26}$ is $C_1$–$C_4$alkyl.

$R_{27}$ is hydrogen or $C_1$–$C_4$alkyl.

$R_{28}$ is hydrogen or $C_1$–$C_4$alkyl.

$R_{29}$ is hydrogen, $C_1$–$C_{12}$alkyl, $C_5$–$C_8$cycloalkyl, unsubstituted or $C_1$–$C_4$alkyl-substituted phenyl, $X_1$ is a group of formula XVIII, XIX or XX

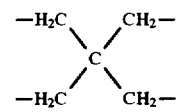 (XVIII)

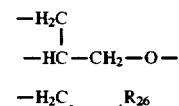 (XIX)

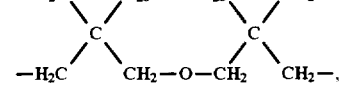 (XX)

$X_2$ is 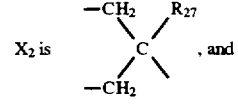, and $X_4$ is 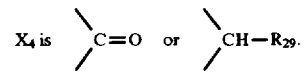

Likewise preferred are the compounds of formula I, wherein $R_4$ is $C_2$–$C_8$alkylene, $C_4$–$C_{12}$alkylene which is interrupted by oxygen; or $C_4$–$C_8$alkenylene, $R_5$ is $C_1$–$C_4$alkyl, $R_6$ is hydrogen, $C_1$–$C_4$alkyl, $C_4$–$C_{18}$alkoxy, $C_5$–$C_8$cycloalkoxy, allyl, propargyl, acetyl or benzyl, $R_7$ is $C_1$–$C_8$alkyl, $R_8$ is $\diagdown N-R_{17}$, $-X_3-\overset{O}{\overset{\|}{C}}-R_{18}-\overset{O}{\overset{\|}{C}}-X_3-$,

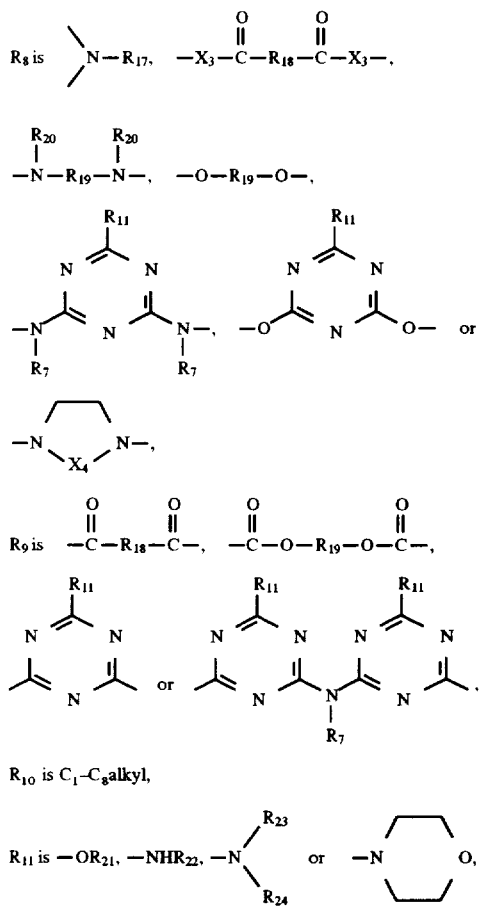

$R_{10}$ is $C_1$–$C_8$alkyl,

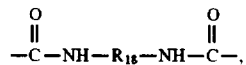

$R_{12}$ and $R_{13}$ are each independently of the other $-\overset{O}{\overset{\|}{C}}-NH-R_{18}-NH-\overset{O}{\overset{\|}{C}}-$, $C_1$–$C_8$alkylene, $C_4$–$C_{12}$-alkylene which is interrupted by oxygen; $C_2$–$C_8$alkenylene, $C_2$–$C_8$alkynylene, $C_2$–$C_{10}$alkylidene, $C_7$–$C_{12}$phenylalkylidene, cyclohexylene or phenylene, $R_{14}$ and $R_{15}$ are each independently of the other hydrogen or $C_1$–$C_4$alkyl, $R_{18}$ is a direct bond, $C_1$–$C_{12}$alkylene, $C_4$–$C_{12}$alkylene which is interrupted by oxygen; $C_2$–$C_8$alkenylene, $C_2$–$C_8$alkylidene, $C_7$–$C_{12}$phenylalkylidene, cyclohexylene or phenylene, $R_{19}$ is $C_1$–$C_{12}$alkylene, $C_2$–$C_{12}$alkylene which is interrupted by oxygen; $C_2$–$C_8$alkenylene, $C_2$–$C_8$alkylidene, $C_7$–$C_{12}$phenylalkylidene, cyclohexylene or phenylene, $R_{20}$ is $C_1$–$C_{12}$alkanoyl or benzoyl, $R_{21}$ is $C_1$–$C_{12}$alkyl, $C_2$–$C_{12}$alkyl which is interrupted by oxygen; $C_2$–$C_{12}$alkenyl, unsubstituted or $C_1$–$C_4$alkyl-substituted cyclohexyl; benzyl or phenyl, $R_{22}$, $R_{23}$ and $R_{24}$ are each independently of one another hydrogen or $C_1$–$C_8$alkyl, $R_{27}$ is hydrogen or $C_1$–$C_4$alkyl, $R_{28}$ is hydrogen or $C_1$–$C_4$alkyl, $R_{29}$ is hydrogen, $C_1$–$C_8$alkyl, cyclohexyl or phenyl, $X_1$ is a group of formula XVIII or XIX

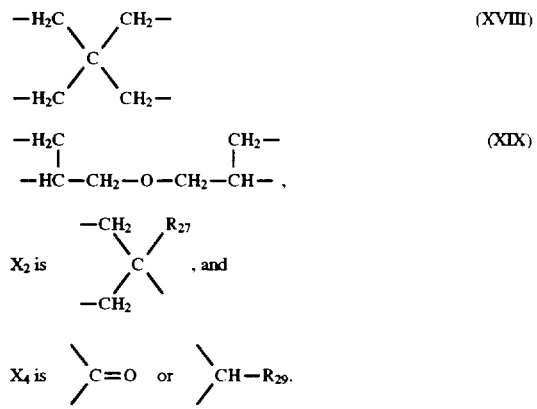

$X_4$ is $\diagdown C=O$ or $\diagdown CH-R_{29}$.

Particularly preferred compounds are those of formula I, wherein

L is a group of formula II $-O-R_3-O-$ (II), $R_4$ is $C_2$–$C_8$alkylene, or $C_4$–$C_8$alkylene which is interrupted by oxygen, $R_5$ is $C_1$–$C_4$alkyl, $R_6$ is hydrogen, $C_1$–$C_4$alkyl, $C_4$–$C_{18}$alkoxy, $C_5$–$C_8$cycloalkoxy, allyl, propargyl, acetyl or benzyl, $R_7$ is $C_1$–$C_8$alkyl,

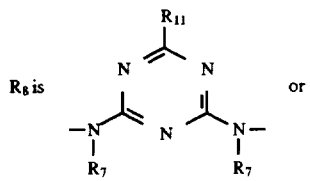

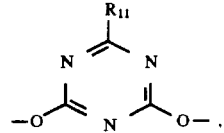

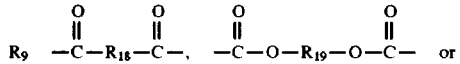

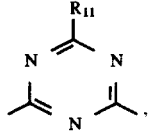

$R_{10}$ is $C_1$–$C_8$alkyl,

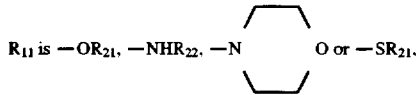

$R_{12}$ and $R_{13}$ are $$-\overset{O}{\underset{\|}{C}}-NH-R_{18}-NH-\overset{O}{\underset{\|}{C}}-,$$

$R_{14}$ and $R_{15}$ are hydrogen.

$R_{18}$ is a direct bond, $C_1$–$C_8$alkylene, or $C_4$–$C_8$alkylene which is interrupted by oxygen.

$R_{19}$ is $C_2$–$C_8$alkylene, or $C_4$–$C_8$alkylene which is interrupted by oxygen.

$R_{21}$ is $C_1$–$C_8$alkyl, $C_4$–$C_{12}$alkyl which is interrupted by oxygen; or cyclohexyl.

$R_{22}$ is $C_1$–$C_8$alkyl.

$R_{27}$ is hydrogen or $C_1$–$C_4$alkyl.

$X_1$ is a group of formula XVIII or XIX $$\begin{matrix}-H_2C & CH_2-\\ & \diagdown\diagup \\ & C \\ & \diagup\diagdown \\ -H_2C & CH_2-\end{matrix} \quad (XVIII)$$

$$\begin{matrix}-H_2C & & CH_2-\\ | & & | \\ -HC-CH_2-O-CH_2-CH- \end{matrix}, \text{ and} \quad (XIX)$$

$X_2$ is 
$$\begin{matrix}-CH_2 & R_{27}\\ \diagdown & \diagup \\ & C \\ \diagup & \diagdown \\ -CH_2 & \end{matrix}$$

Particularly interesting compounds are those of formula I, wherein $R_{10}$ is hydrogen, $C_1$–$C_4$alkyl, $C_4$–$C_{16}$alkoxy, $C_5$–$C_8$cycloalkoxy, allyl, propargyl, acetyl or benzyl.

Compounds of very particular interest are those of formula I, wherein L is a group of formula II $$-O-R_3-O- \quad (II),$$

$R_1$ and $R_2$ are methyl or, together with the linking carbon atom, form a 3,4-dehydrocyclohexylidene ring.

$R_3$ is a group of formula IV, V, VII, VIII, XI, XII, XIV or XVI (IV), (V), (VII)

$R_4$ is ethylene.

$R_6$ is hydrogen or methyl.

$R_7$ is $C_1$–$C_6$alkyl.

(VIII), (XI), (XII), (XIV), (XVI)

$R_{11}$ is $-OR_{21}$, $-HNR_{22}$ or $-N\diagup\diagdown O$, $R_{13}$ is $-\overset{O}{\underset{\|}{C}}-NH-R_{18}-NH-\overset{O}{\underset{\|}{C}}-,$ $R_{14}$ is hydrogen.

$R_{18}$ is a direct bond or $C_1$–$C_8$alkylene.

$R_{21}$ is $C_1$–$C_4$alkyl.

$R_{22}$ is $C_1$–$C_8$alkyl.

$R_{27}$ is hydrogen or methyl.

$X_1$ is a group of formula XVIII

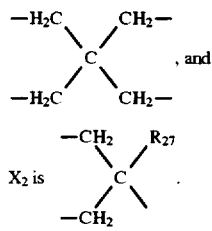

$X_2$ is

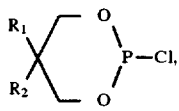

The novel compounds of formula I may be prepared in per se known manner.

The invention furthermore relates to a preferred process for the preparation of compounds of formula I, which comprises reacting a compound of formula XXII

H—L—H           (XXII), wherein L has the given meaning, with a cyclic chlorophosphite of formula XXIII

wherein $R_1$ and $R_2$ have the given meanings.

The reaction is carried out in the melt or in the presence of a suitable organic, polar or apolar aprotic solvent. This reaction is preferably carried out in the presence of a base in the temperature range from $-20°$ C. to the boiling point of the solvent, more particularly from $20°$ to $150°$ C.

Bases such as amines can simultaneously also be used as solvent.

The base can be used in various amounts, from catalytic via stoichiometric amounts up to an excess of several times the molar amount with respect to the compounds of formula XXII or the compounds of formula XXIII employed. The hydrogen chloride formed during the reaction is, if appropriate, converted via the base into chloride, which can be removed by filtration and/or washing with a suitable aqueous or solid phase; a second, water-immiscible solvent can also be employed here. The products are expediently isolated by evaporating the organic phase and drying the residue.

Suitable solvents for carrying out the reaction include hydrocarbons (typically mesitylene, toluene, xylene, hexane, pentane or other petroleum ether fractions), halogenated hydrocarbons (typically di- or trichloromethane, 1,2-dichloroethane, 1,1,1-trichloroethane or chlorobenzene), ethers (typically diethyl ether, dibutyl ether or tetrahydrofuran), ketones (typically acetone, ethyl methyl ketone, diethyl ketone, methyl propyl ketone or cyclohexanone), furthermore acetonitrile, butyl acetate, dimethyl formamide, dimethyl sulfoxide or N-methylpyrrolidone.

Suitable bases include primary, secondary and, preferably, tertiary amines (typically trimethylamine, triethylamine, tributylamine, N,N-dimethylaniline, N,N-diethylaniline or pyridine), hydrides (typically lithium hydride, sodium hydride or potassium hydride) or alcoholates (typically sodium methanolate).

If hydrides (e.g. sodium hydride, sodium borohydride or lithium aluminium hydride), alkali metals, alkali metal hydroxides or sodium methanolate are used as bases, the corresponding alcoholate of the compound of formula XXIII can first be formed; any reaction product formed (for example water or methanol) is removed by distillation (typically as an azeotrope with toluene) before the reaction with the compound of the formula XXII.

The preparation of the compounds of formulae XXII and XXIII is known.

The HALS compounds of XXII are known or can be prepared by per se known processes such as those disclosed, inter alia, in U.S. Pat. No. 3,974,127, U.S. Pat. No. 4,279,804; U.S. Pat. No. 4,798,836; U.S. Pat. No. 4,883,870; U.S. Pat. No. 5,198,546; U.S. Pat. No. 4,731,448 or EP-A-0 047 967.

The chlorophosphites of formula XXIII are known or can be prepared by per se known processes such as those disclosed in Houben-Weyl, Methoden der Organischen Chemie, Vol. El, pages 373–376 (1982); J. H. R. O. Day et al., Inorganic Chemistry 31 (7), 1279–1285 (1992); or B. Costisella et al., Journal für praktische Chemie, Vol. 314 (3–4), pages 532–542 (1972).

The novel compounds of formula I are suitable for stabilising organic materials against oxidative, thermal or light-induced degradation.

Illustrative examples of such materials are

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (uncrosslinked or crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/ propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or (x-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or (x-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with diglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyether imides, polyester imides, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Accordingly the invention also relates to compositions comprising (a) an organic material susceptible to oxidative, thermal or light-induced degradation, and (b) at least one compound of formula L The organic materials to be protected are preferably natural, semi-synthetic or, more particularly, synthetic polymers. Thermoplastic polymers are particularly preferred, more particularly PVC or polyolefins, most preferably polyethylene and polypropylene.

To be highlighted in particular is the action of the novel compounds against thermal and oxidative degradation, in particular when subjected to heat, as is the case when the thermoplasts are processed. The novel compounds are thus admirably suited for use as processing stabilisers.

The compounds of formula I are preferably added to the material to be stabilised in amounts of 0.01 to 10%, typically of 0.01 to 5%, preferably of 0.025 to 3%, more preferably of 0.025 to 1%, based on the weight of the organic material to be stabilised.

In addition to the compounds of formula I the novel compositions may contain further costabilisers such as the following:

1. Antioxidants 1.1. Alkylated monoiphenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl- 4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example (α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis|4-methyl-6-(α-methylcyclohexyl)phenol|, 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis|6-(α-methylbenzyl)-4-nonylphenol|, 2,2'-methylenebis|6-(α,α-dimethylbenzyl)-4-nonylphenol|, 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis|3,3-bis(3'-tert-butyl-4'-hydroxyphenyl)butyrate|, bis(3-tert-butyl-4-hydroxy-5-methyl-phenyl)dicyclopentadiene, bis|2-(3'-tert-butyl-2'-hydroxy-5'-methylbenzyl)-6-tert-butyl-4-methylphenyl/terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7. O—, N— and S-benzyl compounds, for example 3,5,3',5'-tetra-tert-butyl-4,4'-dihydroxy-dibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis|4-(1,1,3,3-tetramethylbutyl)phenyl|-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6- trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis (octylmercapto)-6-(3,5-di-tert-butyl-4-hydroxyanilino)-1,3, 5-triazine, 2-octylmercapto-4,6-bis(3,5-di-tert-butyl-4-hydroxyanilino)-1,3,5-triazine, 2-octylmercapto-4,6-bis(3, 5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-di-methylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis|(2-methylphenyl)amino|ethane, 1,2-bis(phenylamino) propane, (o-tolyl)biguanide, bis|4-(1',3'-dimethylbutyl) phenyl|amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazine, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1, 1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl) phenyl)-5-chlorobenzotriazole, 2-(3'-tert-butyl-5'-|2-(2-ethylhexyloxy)carbonylethyl|-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tertbutyl-5'-|2-(2-ethylhexyloxy)carbonylethyl- 2-ethyl|-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole 2,2'-methylenebis|4-(1,1,3,3-tetramethylbutyl)-6-benzotriazol-2-ylphenol|; the transesterification product of 2-|3'-tert-butyl-5'-(2-methoxycarbonylethyl)-2'-hydroxyphenyl|-2H-benzotriazole with polyethylene glycol 300; |R—CH₂CH₂—COO(CH₂)₃-t₂, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl) resorcinol, benzoyl resorcinol, 2,4-ditertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl (α-cyano-β,β-diphenylacrylate, isooctyl (α-cyano-β,β-diphenylacrylate, methyl α-carbomethoxycinnamate, methyl α-cyano-β-methyl-p-methoxycinnamate, butyl (α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis|4-(1,1,3,3-tetramethylbutyl)phenol|, such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)- 2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro|4,5|decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl )-1,3,5-triazine, and 1,2-bis(3-aminopropylamino)ethane, the condensate of 2-chloro-4,6-bis(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro|4,5|decane-2,4-dione, 3-dodecyl-1-(2,2,6,6-tetramethyl-4-piperidyl)pyrrolidine-2, 5-dione, 3-dodecyl-1-(1,2,2,6,6-pentamethyl-4-piperidyl) pyrrolidine-2,5-dione, a mixture of 4-hexadecyloxy and 4-stearyloxy-2,2,6,6-tetramethylpiperidine, a condensation product of N,N'-bis-(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. |136504-96-6|); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro|4,5| decane, a reaction product of 7,7,9,9-tetramethyl-2-cycloundecyl-1-oxa-3,8-diaza-4-oxospiro |4,5|decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and the mixture thereof with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxy phenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy 4-octyloxyphenyl)-4,6-bis(4-methylphenyl)-1,3,5-triazine, 2-(2-hydroxy-4-dodecyloxyphenyl)4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-|2-hydroxy-4-(2-hydroxy-3-butyloxy-propoxy)phenyl|-4,6-bis(2,4-dimethyl)-1,3,5-triazine, 2-|2-hydroxy-4-(2-hydroxy-3-octyloxy-propyloxy)phenyl|-4,6-bis(2,4-dimethyl)-1,3,5-triazine, 2-|4-(dodecyloxy/tridecyloxy-2-hydroxypropoxy)-2-hydroxy-phenyl|-4,6-bis(2,4-dimethylphenyl)-1,3,5-triazine, 2-|2-hydroxy-4-(2-hydroxy-3-dodecyloxy-propoxy)phenyl|-4,6-bis(2,4-dimethylphenyl)1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6tris|2-hydroxy-4-(3-butoxy-2-hydroxy-propoxy)phenyl|1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylat-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4- methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, e.g. calcium stearate, zinc stearate, magnesium behenate, magnesium stearate, sodium ricinoleate and potassium palmitate, antimony pyrocatecholate or tin pyrocatecholate.

11. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass beads, asbestos, talc, kaolin, mica, barium sulfate, metal oxides and hydroxides, carbon black, graphite, sawdust or fibers of other natural products, synthetic fibers.

13. Other additives, for example, plasticisers, lubricants, emulsifiers, pigments, rheology additives, catalysts, flow-control agents, fluorescent whitening agents, flame-proofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. N 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butylbenzofuran-2-one, 5,7-di-tert-butyl-3-[4-(2-stearoyloxyethoxy)phenyl/benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one.

With the exception of the benzofuranones listed in item 14, the costabilisers are added typically in concentrations of 0.01 to 10%, based on the total weight of the material to be stabilised.

Further preferred compositions comprise, besides component (a) and the compounds of formula I, further additives, preferably phenolic antioxidants, light stabilisers and/or processing stabilisers.

Particularly preferred additives are phenolic antioxidants (item 1 in the list), sterically hindered amines (item 2.6 in the list), phosphites and phosphonites (item 4 in the list) and peroxide scavengers (item 8 in the list).

Further additives (stabilisers) which are also particularly preferred are benzofuran-2-ones, such as those disclosed, inter alia, in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 and EP-A-0 591 102.

Examples of such benzofuran-2-ones are compounds of formula

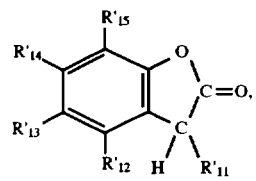

wherein

R'$_{11}$ is an unsubstituted or substituted carbocyclic or heterocyclic aromatic ring system;

R'$_{12}$ is hydrogen;

R'$_{14}$ is hydrogen, alkyl of 1 to 12 carbon atoms, cyclopentyl, cyclohexyl or chloro;

R'$_{13}$ has the meaning of R'$_{12}$ or R'$_{14}$ or is a radical of formula

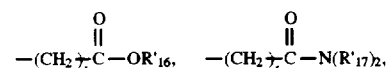

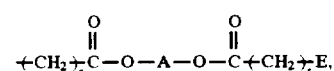

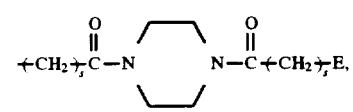

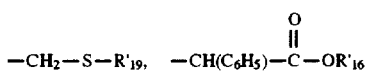

or —D—E, wherein

R'$_{16}$ is hydrogen, alkyl of 1 to 18 carbon atoms, alkyl of 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals having a total of at most 18 carbon atoms;

s is 0, 1 or 2;

substituents R'$_{17}$ are each independently of one another hydrogen, alkyl of 1 to 18 carbon atoms, cyclopentyl, cyclohexyl, phenyl; phenyl which is substituted by 1 or 2 alkyl radicals having a total of at most 16 carbon atoms, a radical of formula —C$_2$H$_4$OH, —C$_2$H$_4$—O—C$_r$H$_{2r+1}$ or

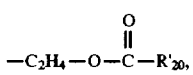

or, together with the linking nitrogen atom, form a piperidine or morpholine radical;

t is 1 to 18;

R'$_{20}$ is hydrogen, alkyl of 1 to 22 carbon atoms, or cycloalkyl of 5 to 12 carbon atoms;

A is alkylene of 2 to 22 carbon atoms which may be interrupted by nitrogen, oxygen or sulfur;

R'$_{18}$ is hydrogen, alkyl of 1 to 18 carbon atoms, cyclopentyl, cyclohexyl, phenyl; phenyl which is substituted by 1 or 2 alkyl radicals having a total of at most 16 carbon atoms, or benzyl;

R'$_{19}$ is alkyl of 1 to 18 carbon atoms;

D is —O—, —S—, —SO—, —SO$_2$— or —C(R'$_{21}$)$_2$—;
substituents R'$_{21}$ are each independently of one another hydrogen, C$_1$–C$_{16}$alkyl, the two R'$_{21}$ radicals together containing 1 to 16 carbon atoms, and R'$_{21}$ is furthermore phenyl or a radical of formula

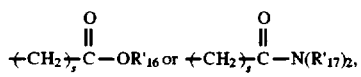

wherein s, R'$_{16}$ and

R'$_{17}$ are as defined above;

E is a radical of formula

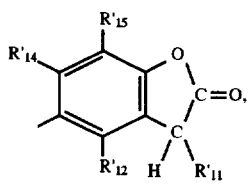

wherein R'$_{11}$, R'$_{12}$ and R'$_{14}$ are as defined above; and

R'$_{15}$ is hydrogen, alkyl of 1 to 20 carbon atoms, cyclopentyl, cyclohexyl, chloro, or a radical of formula

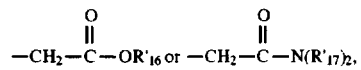

wherein R'$_{16}$ and R'$_{17}$ are as defined above, or R'$_{15}$ and R'$_{14}$, taken together, form a tetramethylene radical.

Preferred benzofuran-2-ones are those wherein R'$_{13}$ is hydrogen, alkyl of 1 to 12 carbon atoms, cyclopentyl, cyclohexyl, chloro or a radical of formula

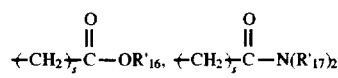

or —D—E, wherein s, R'$_{16}$, R'$_{17}$, D and E are as defined above, and R'$_{16}$ is preferably hydrogen, alkyl of 1 to 18 carbon atoms, cyclopentyl or cyclohexyl.

Preferred benzofuran-2-ones are also those wherein R'$_{11}$ is phenyl or phenyl which is substituted by 1 or 2 alkyl radicals having a total of at most 12 carbon atoms; R'$_{12}$ is hydrogen; R'$_{14}$ is hydrogen or alkyl of 1 to 12 carbon atoms; R'$_{13}$ is hydrogen, alkyl of 1 to 12 carbon atoms,

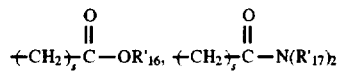

or —D—E; R'$_{15}$ is hydrogen, alkyl of 1 to 20 carbon atoms,

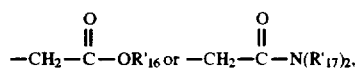

or R'$_{15}$ and R'$_{14}$, taken together, form a tetramethylene radical, in which groups s, R'$_{16}$, R'$_{17}$, D and E are as defined at the outset.

Particularly interesting benzofuran-2-ones are also those wherein R'$_{13}$ is hydrogen, alkyl of 1 to 12 carbon atoms or —D—E; R'$_{12}$ and R'$_{14}$ are each independently of the other hydrogen or alkyl of 1 to 4 carbon atoms; R'$_{15}$ is alkyl of 1 to 20 carbon atoms, and D and E are as defined at the outset.

Of particular interest are finally also those benzofuran-2-ones, wherein R'$_{13}$ is alkyl of 1 to 4 carbon atoms or —D—E; R'$_{12}$ and R'$_{14}$ are hydrogen; R'$_{15}$ is alkyl of 1 to 4 carbon atoms, cyclopentyl or cyclohexyl, D is a —C(R'$_{21}$)$_2$— group, and E is a radical of formula

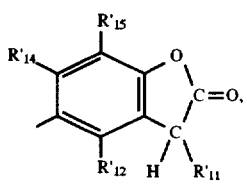

the substituents R'$_{21}$ being identical or different and are each alkyl of 1 to 4 carbon atoms, and R'$_{11}$, R'$_{12}$, R'$_{14}$ and R'$_{15}$ are as defined above.

The amount of benzofuran-2-ones additionally employed can vary within wide limits. They can be present in the novel compositions typically in amounts of 0.0001 to 5% by weight, preferably of 0.001 to 2% by weight, most preferably of 0.01 to 2% by weight.

The compounds of formula I and any further additives are incorporated into the polymeric organic material by known methods, typically before or during shaping or alternatively by applying the dissolved or dispersed compounds to the polymeric organic material, with subsequent evaporation of the solvent, when used. The compounds of formula I can also be added to the materials to be stabilised in the form of a masterbatch which contains these compounds in a concentration of typically 2.5 to 25% by weight.

The compounds of formula I can also be added before or during polymerisation or before crosslinking.

The compounds of formula I can be incorporated into the material to be stabilised in pure form or encapsulated in waxes, oils or polymers.

The compounds of formula I can also be sprayed onto the polymer to be stabilised. They are able to dilute other additives (e.g. the conventional additives mentioned above) or their melts, so that they can also be sprayed onto the polymer to be stabilised together with these additives. Application by spraying during deactivation of the polymerisation catalysts is particularly advantageous, in which case the steam used for the deactivation may be used for spraying.

In the case of spherically polymerised polyolefins, the compounds of formula I may be usefully applied by spraying, if desired together with other additives.

The materials stabilised in this manner can be used in a very wide range of forms, typically including sheets, filaments, ribbons moulded articles, profiles or as binders for paints, adhesives or putties.

As already mentioned, the organic materials to be protected are preferably organic polymers, more particularly synthetic polymers. It is especially useful to protect thermoplastic materials and, preferably, polyolefins. To be highlighted in this connection is in particular the excellent action of the compounds of formula I as processing stabilisers (heat stabilisers). For this purpose, they are usefully added to the polymer before or during processing. However, other polymers (e.g. elastomers) or lubricants or hydraulic fluids can also be stabilised against degradation, such as light-induced or thermo-oxidative degradation. Examples of elastomers will be found in the above list of possible organic materials.

Suitable lubricants and hydraulic fluids may be based on mineral or synthetic oils, or mixtures thereof. The lubricants are known to the person skilled in the art and are described in the relevant technical literature, for example in Dieter Klamann, "Schmierstoffe und verwandte Produkte" (Verlag Chemie, Weinheim, 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie", Vol. 13, pages 85–94 (Verlag Chemie, Weinheim, 1977).

Accordingly, a preferred embodiment of this invention is the use of compounds of formula I for stabilising organic materials against oxidative, thermal or light-induced degradation.

The novel compounds of formula I are distinguished by their markedly good stability to hydrolysis and their advantageous colour behaviour, i.e. minor discoloration of the organic materials during processing.

Organic materials stabilised with the novel compounds are particularly well protected against light-induced degradation.

Accordingly, the invention also relates to a process for stabilising an organic material against oxidative, thermal or light-induced degradation, which process comprises incorporating in, or applying to, said material at least one compound of formula I.

The following Examples illustrate the invention in greater detail. Parts and percentages are by weight.

EXAMPLE 1

Preparation of compound (101) (Table 1)

2.90 g (17.0 mmol) of 2-chloro-5,5-dimethyl-1,3-dioxaphosphorinane |Houben-Weyl, Methoden der Organischen Chemie, Vol. E1, pages 373–376 (1982)| are slowly added dropwise at room temperature to a suspension, stirred under nitrogen, consisting of 1.70 g (8.50 mmol) of 1-(2-hydroxyethyl)-4-hydroxy-2,2,6,6-tetramethylpiperidine |U.S. Pat. No. 4,731,448, Ciba-Geigy AG| and 5.95 ml (42.5 mmol) of triethylamine in 17 ml of toluene. The reaction mixture is then stirred for a further ¾ h at room temperature, and 10 ml of hexane are then added. The precipitated triethylamine hydrochloride is removed by filtration and the filtrate is concentrated on a vacuum rotary evaporator. The residue is dried under a high vacuum, to give 3.3 g (89%) of compound (101) in the form of a colourless oil (Table 1).

In general accordance with the procedure of Example 1, compound (102) is obtained by starting from N-(2,2,6,6-tetramethylpiperidin-4-yl)diethanolamine (201) |EP-A-0 047 967, Goodrich Company, Example II, page 9|

HO—CH₂—CH₂—N—CH₂—CH₂—OH     (201)

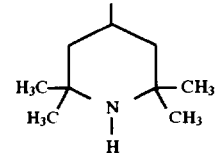

instead of from 1-(2-hydroxyethyl)-4-hydroxy-2,2,6,6-tetramethylpiperidine.

EXAMPLE 2

Preparation of compound (103) (Table 1)

A) Preparation of the HALS diols:

a) A steel autoclave is charged with 42.47 g (0.20 mol) of 4-n-butylamino-2,2,6,6-tetramethylpiperidine |EP-A-302 020, Example 1, page 4|, 3 ml of concentrated hydrochloric acid and 300 ml of methanol. The autoclave is blanketed with nitrogen. 26.5 g (0.60 mol) of ethylene oxide are then introduced under pressure and the entire reaction mixture is heated to 150° C. The pressure in the autoclave is 10 bar. After 30 hours the reaction mixture is cooled to room temperature. About 250 ml of methanol are distilled off and the residue is poured into an aqueous saturated solution of sodium hydrogen carbonate and extracted three times with ethyl acetate. The organic phases are washed with an aqueous solution of saturated sodium chloride, dried over sodium sulfate and concentrated on a vacuum rotary evaporator. Chromatography of the residue over silica gel using the solvent system hexane/ethyl acetate 3:1 to 1:1 and ethyl acetate gives 31.5 g (53%) of 2-(n-butyl-|1-(2-hydroxyethyl)-2,2,6,6-tetramethylpiperidine-4-yl|amino) ethanol (compound (202)) in the form of a pale yellow oil.

Analysis calculated: C 67.95%; H 12.08%; N 9.32%
found: C 67.31%; H 11.98%; N 9.10%

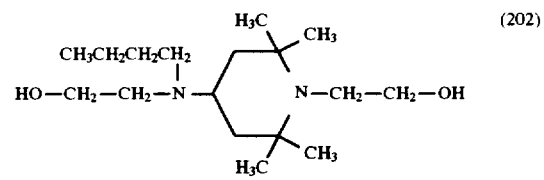

b) In general accordance with the procedure of Example 2Aa, the HALS diol (203) is prepared starting from the known 4-amino-1,2,2,6,6-pentamethylpiperidine |Beilstein EII, Vol. 22, page 321| with ethylene oxide, m.p. 57°–64° C.

Analysis calculated: C 65.07%; H 11.70%; N 10.84%
found: C 64.68%; H 11.43%; N 10.69%

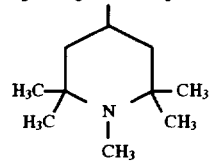
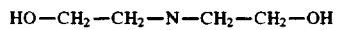
(203)

c) In general accordance with the procedure of Example 2Aa, the HALS diol (204) is prepared starting from the known bis(2,2,6,6-tetramethylpiperidin-4-yl)sebacinate [®Tinuvin 770, Ciba-Geigy AG, U.S. Pat. No. 4,396,769] with ethylene oxide. Yield: 67%, m.p. 59°–62° C., in the form of a white powder.

Analysis calculated: C 67.57%; H 10.63%; N 4.92%
found: C 67.37%; H 10.67%; N 4.78%

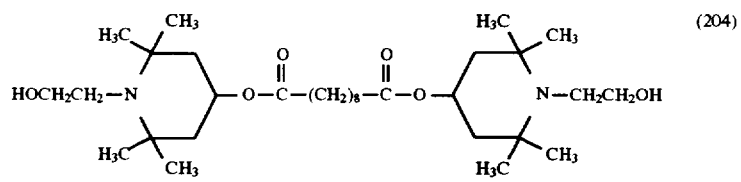
(204)

d) 1.99.4 g (0.46 mol) of 4-n-butylamino-2,2,6,6-tetramethylpiperidine [EP-A-302 020, Example 1, page 4]

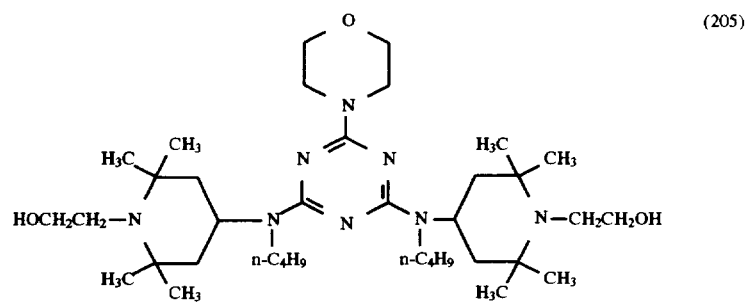
(205)

are added dropwise at 15° C. under nitrogen to a solution of 42.4 g (0.23 mol) of cyanuric chloride in 280 ml of xylene. The reaction mixture is stirred for 30 minutes at room temperature. After subsequent heating, to c. 55° C., a solution of 20 g (0.50 mol) of sodium hydroxide in 50 ml of water is added dropwise. When the addition is complete, the reaction mixture is stirred for a further 30 minutes at 55° C. The aqueous phase is separated and the mixture is heated to 90° C. while simultaneously adding dropwise 24 g (0.27 mol) of morpholine and a solution of 10 g (0.25 mol) of sodium hydroxide in 25 ml of water. The water is distilled off as an azeotrope. 50 ml of xylene are then removed under a slight vacuum (115° C./0.7 torr). The reaction mixture is cooled to c. 50° C. and washed twice with water. The organic phases are combined and filtered over hyflo. After addition of 50 ml of water and cooling to 5° C., 110 g (82%) of 2-N-morpholino-4,6-bis[N-n-butyl-(2,2,6,6-tetramethylpiperidine-4-yl)amino]-1,3,5-triazine crystallise in the form of a white powder, m.p. 112°–114° C.

Analysis calculated: C 67..53%; H 10.65%; N 19.09%
found: C 67.28%; H 10.70%; N 19.06%

2. In general accordance with the procedure of Example 2Aa, the HALS diol (205) is prepared starting from 2-N-morpholino-4,6-bis[N-n-butyl-(2,2,6,6-tetramethyl-piperidin-4-yl)amino]-1,3,5-triazine (Example 2Ad1) with ethylene oxide, m.p. 114°–117° C.

Analysis calculated: C 65.84%; H 10.45%; N 16.60%
found: C 65.86%; H 10.33%; N 16.01% e) 1. A 200 ml sulfonation flask is charged with 40.48 g (0.14 mol) of bis(2,2,6,6-tetramethyl-piperidin-4-yl)amine [EP-A-336 895, Ciba-Geigy] and 11.4 g (0.14 mol) of a 36% aqueous solution of formaldehyde. 25.8 g (0.56 mol) of formic acid are added dropwise at room temperature. The temperature in the flask rises to 70° C. with evolution of $CO_2$. The reaction mixture is stirred until it has cooled to room temperature. The aqueous phase is then saturated with potassium carbonate and the reaction mixture is extracted three times with chloroform. The organic phases are combined, dried over potassium carbonate and concentrated on a vacuum rotary evaporator. Chromatography of the residue over silica gel using the solvent system hexane/dichloromethane 9:1+5% triethylamine gives 21 g (49%) of the methyl-bis(2,2,6,6-tetramethyl-piperidin-4-yl)amine, m.p. 51°–53° C., in the form of a white powder.

$^1$H-NMR (300 MHz, $CDCl_3$): δ=2.25 ppm (s, 3H) methyl group at nitrogen.

2. In general accordance with the procedure of Example 2Aa, the HALS diol (206) is prepared starting from the methyl-bis(2,2,6,6-tetramethyl-piperidin-4-yl)amine (Example 2Ae1) with ethylene oxide.

Analysis calculated: C 69.47%; H 11.91%; N 10.57%
found: C 68.31%; H 12.16%; N 10.50%

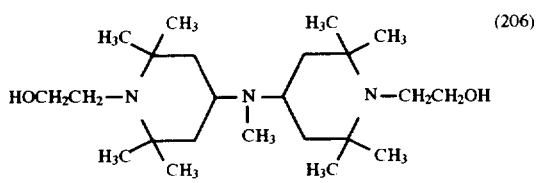

f) The HALS diol (207) is known and the preparation thereof is disclosed in U.S. Pat. No. 4,210,576 (Montedison), page 5, Example 1.

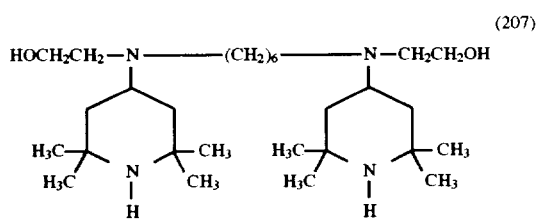

g)1. 63.5 g (0. 195 mol) of a 21% solution of sodium ethylate in toluene are added dropwise at room temperature under nitrogen to a solution of 69.7 g (0.13 mol) of 2,4-bis |N-(2,2,6,6-tetramethyl-4-piperidinyl)butylamino|-6-chloro-1,3,5-triazine |EP-A-314 472, Sankyo| in 400 ml of toluene. The reaction mixture is then refluxed for 20 hours. After cooling to room temperature, the reaction mixture is washed successively with water, 1N sodium hydrogen carbonate solution and saturated sodium chloride solution. The organic phases are combined, dried over potassium carbonate and concentrated on a vacuum rotary evaporator. Crystallisation of the residue from acetonitrile gives 52.2 g (74%) of 2-ethoxy-4,6-bis|N-(2,2,6,6-tetramethyl- 4-piperidinyl)butylamino|-1,3,5-triazine, m.p. 95°–104° C., in the form of a white powder. $^1$H-NMR (300 MHz, CDCl$_3$): δ=4.345 ppm (q, J=7 Hz) —OCH$_2$CH$_3$.

2. A 1 l autoclave is charged with 38.5 g (0.07 mol) of 2-ethoxy-4,6-bis|N-(2,2,6,6-tetramethyl-4-piperidinyl)butylamino|-1,3,5-triazine (Example 2Ag1), 140 ml of ethanol and 70 ml of water. The autoclave is blanketed with nitrogen. 12.4 g (0.28 mol) of ethylene oxide are introduced under pressure and the reaction mixture is heated to 90° C. (pressure=2 bar). After 2 hours, the mixture is cooled to 30° C. and a further 12.4 g (0.28 mol) of ethylene oxide are introduced under pressure. The reaction mixture is heated to 100° C. and kept at this temperature for 3 hours (pressure =3 bar). After cooling to room temperature, the reaction mixture is concentrated on a vacuum rotary evaporator. The residue is dissolved in 100 ml of acetonitrile and filtered hot. 40 g (90%) of the HALS diol (208), m.p. 160°–170° C., crystallise in the form of a white powder from the cooled filtrate.

Analysis calculated: C 66.31%; H 10.65%; N 15.47% found: C 66.23%; H 10.61%; N 15.34% h) 1. 16.5 g (0.21 mol) of acetyl chloride are added dropwise at 12°–13° C. under nitrogen to a solution of 42.5 g (0.20 mol) of 4-n-butylamino-2,2,6,6-tetramethylpiperidine |EP-A-302 020, Example 1, page 4| and 50 ml (36.3 g; 0.36 mol) of triethylamine in 300 ml of toluene. The reaction mixture is stirred for 3 hours at room temperature. The precipitated triethylamine hydrochloride is removed by filtration and the filtrate is concentrated on a vacuum rotary evaporator. Distillation of the residue (90°–92° C., 0.05 mbar) gives 38.7 g (76%) of N-n-butyl-N-(2,2,6,6-tetramethyl-4-piperidinyl)acetamide in the form of a viscous oil.

2. In general accordance with the procedure of Example 2Ag2, 27.2 g of crude product are obtained starting from 25.4 g (0.10 mol) of N-n-butyl-N-(2,2,6,6-tetramethyl-4-piperidinyl)acetamide |Example 2Ah1| and 17.6 g (0.40 mol) of ethylene oxide in 100 ml of water and 100 ml of ethanol. Chromatography over silica gel using the solvent system ethyl acetate/ethanol/triethylamine =30: 1:1 gives 17.2 (58%) of the desired N-n-butyl-N-|1-(2-hydroxyethyl)-2,2,6,6-tetramethylpiperidin-4-yl|acetamide in the form of a viscous oil which solidifies during storage; m.p. 72°–82° C.

Analysis calculated: C 68.41%; H 11.48%; N 9.39% found: C 67.99%; H 11.96%; N 9.14%

3. A solution of 12.6 g (42.2 mmol) of N-n-butyl-N-|1-(2-hydroxyethyl)-2,2,6,6-tetramethylpiperidin-4-yl| acetamide |Example 1bη2| in 180 ml of 2N hydrochloric acid is refluxed for 48 hours. The reaction mixture is then cooled 0°–5° C. and, after addition of 40 ml of 30% sodium hydroxide solution, extracted twice with toluene. The organic phases are washed with water, combined, dried over sodium sulfate and concentrated on a vacuum rotary evaporator. Chromatography of the residue over silica gel with the solvent system ethyl acetate/ethanol/triethylamine=50:2:1 gives 8.1 g (68%) of 2-(4-n-butylamino-2,2,6,6-tetramethylpiperidin-1-yl) ethanol (208) in the form of a white powder, m.p. 106°–111° C.

Analysis calculated: C 70.26%; H 12.58%; N 10.92% found: C 70.42%; H 12.85%; N 11.00%

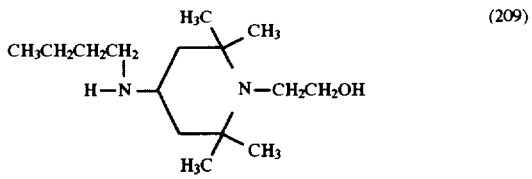

i) A round-bottomed flask, equipped with magnetic stirrer and condenser, is charged with 833 g (5.30 mol) of 4-hydroxy-2,2,6,6-tetramethylpiperidine and 418 g (1.05 mol) of 2-butyne-1,4-diol-ditosylate |C.A. Registry No. 6337-59-3| in 3.6 1 of acetonitrile under argon. The reaction mixture is refluxed overnight, then cooled, poured on ice and extracted repeatedly with ethyl acetate. The organic phases are combined, dried over sodium sulfate and concentrated

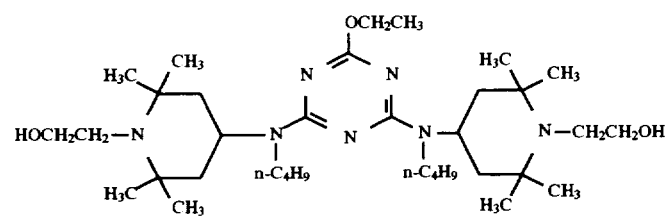

on a vacuum rotary evaporator. Crystallisation of the residue from ethanol gives 295 g (76%) of 1,4-bis(4-hydroxy-2,2, 6,6-tetramethylpiperidin-1-yl)but-2-yne (209), m.p. 203.4° C., in the form of white crystals.

Analysis calculated: C 72.48%; H 11.06%; N 7.68% found: C 72.52%; H 11.12%; N 7.75%

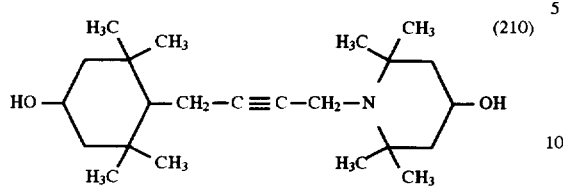
(210)

k) 1. A solution of 5.4 g (29 mmol) of cyanuric chloride in 40 ml of dioxane are added dropwise at 40° C. to a solution, stirred under nitrogen, of 12.8 g (60 mmol) of 4-(2-hydroxyethylamino)-1,2,2,6,6-pentamethylpiperidine [U.S. Pat No. 3,904,581, Sankyo] in 120 ml of dioxane. After the addition is complete (c. 15 minutes), the reaction mixture is refluxed for 3 hours. The suspension obtained is cooled to room temperature and the precipitated product is isolated by filtration, taken up in a cold solution of ammonia and filtered again. Crystallisation of the residue from toluene gives 11.0 g (71%) of 2,4-bis[2-hydroxy-N-(1,2,2,6,6-pentamethyl-4-piperidinyl)ethylamino]-6-chloro-1,3,5-triazine, m.p. 166°–176° C., in the form of a white powder.

Analysis calculated: C 60.03%; H 9.33%; N 18.15%; Cl 6.56% found: C 60.01%; H 9.36%; N 17.97%; Cl 6.70%

2. A solution of 5.40 g (10.0 mmol) of 2,4-bis[2-hydroxy-N-(1,2,2,6,6-pentamethyl-4-piperidinyl)ethylamino]-6-chloro-1,3,5-triazine (Example 2Ak1) and 2.0 g (15.0 mmol) of n-octylamine in 100 ml of dioxane is refluxed under nitrogen for 6 hours. The dioxane is then distilled off and the residue is poured into a 10% aqueous solution of sodium carbonate and then extraced with ethyl acetate. The organic phases are combined, dried over magnesium sulfate and concentrated on a vacuum rotary evaporator. Chromatography of the residue over silica gel using the solvent system ethyl acetate/ethanol/triethylamine 20:1:1 gives 5.5 g (87%) of the HALS diol (211).

m.p. 55–62.

Analysis calculated: C 66.41%; H 10.83%; N 17.70% found: C 65.90%; H 11.08%; N 17.58%

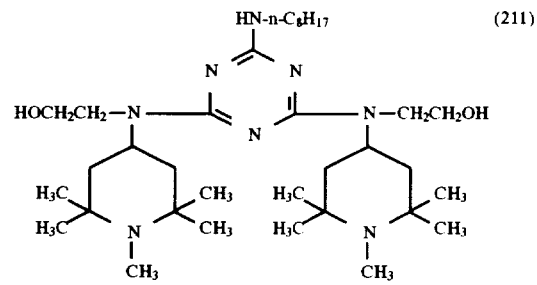
(211)

l) In general accordance with the procedure of Example 2Ak2, the HALS diol (212) is prepared with 4-butylamino-1,2,2,6,6-pentamethylpiperidine instead of with n-octylamine.

m.p. 215°–225° C.

Analysis calculated: C 67.45%; H 10.91%; N 17.27% found: C 66.94%; H 11.06%; N 17.12%

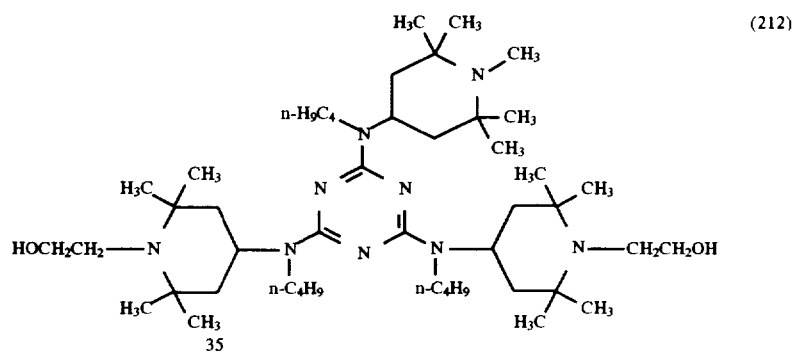
(212)

m) The HALS diol (213) is known and is disclosed in DE-A-2 233 121 (Sankyo, Example 7, page 21, lines 1 and 2).

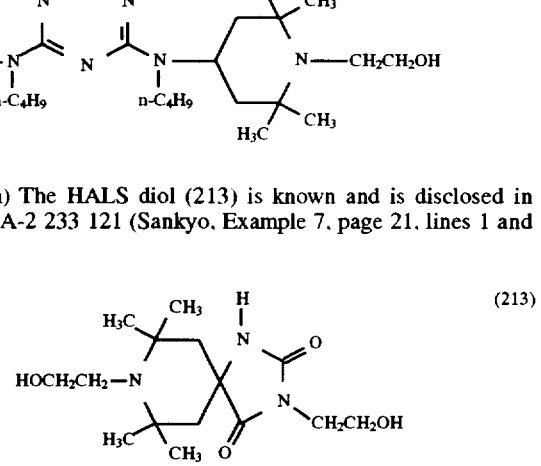
(213)

n) The HALS diol (214) is known and is disclosed in U.S. Pat. No. 4,569,997 (Ciba-Geigy, Example 1, column 14).

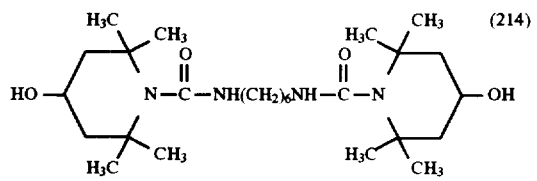
(214)

o) A 1 l autoclave is charged with 12.1 g (47.0 mmol) of 9-aza-3-hydroxymethyl-3,8,8,10,10-pentamethyl-1,5-dioxospiro[5.5]undecane (DE-A-2 353 538, Sankyo, Example 1, page 38), 50 ml of ethanol and 50 ml of water. The autoclave is blanketed with nitrogen. 8.2 g (188 mmol) of ethylene oxide are then introduced under pressure and the reaction mixture is heated to 90° C. (pressure=2 bar). After 2 hours, the reaction mixture is cooled to 30° C. and a further 8.2 g (188 mmol) of ethylene oxide are introduced under pressure. The reaction mixture is heated to 100° C. and kept at this temperature for 3 hours (pressure=3 bar). After cooling to room temperature, the reaction mixture is concentrated on a vacuum rotary evaporator. The residue is dissolved in ethyl acetate and chromatographed over silica gel using ethyl acetate as eluant. Crystallisation of the pure fractions from toluene/hexane=9:1 gives 11.15 g (79%) of the HALS diol (215), m.p. 110°–115° C., in the form of a white powder.

Analysis calculated: C 63.76%; H 10.37%; N 4.65% found: C 64.04%; H 10.32%; N 4.45%

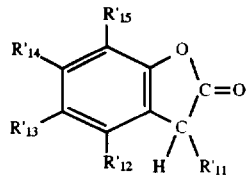
(215)

p) The HALS diol (216) is also known and the preparation thereof is disclosed in JP-A-57 21 368 (Adeka Argus, Example 7).

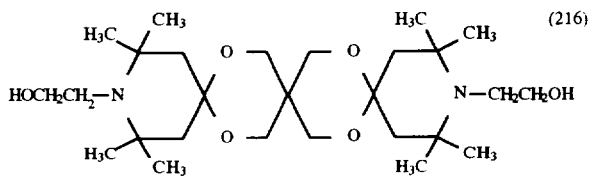
(216)

B) 1.24 g (7.35 mmol) of 2-chloro-5,5-dimethyl-1,3-dioxaphosphorinane |Houben-Weyl, Methoden der Organischen Chemie, Vol. El, pages 373–376 (1982)| are slowly added dropwise at room temperature to a solution, stirred under nitrogen, of 2.43 g (3.60 mmol) of 2N-morpholino-4,6-bis-|N-n-butyl-(N-2'-hydroxyethyl-2,2,6,6-tetramethylpiperidin-4-yl)amino|-1,3,5-triazine |Example 2Ad, compound (205)| and 2.5 ml (18.0 mmol) of triethylamine in 24 ml of toluene. The reaction mixture is then stirred for a further 1 hour at 40° C. The precipitated triethylamine hydrochloride is removed by filtration and the filtrate is concentrated on a vacuum rotary evaporator. Crystallisation of the residue from acetonitrile gives 2.75 g (81%) of compound (103) (Table 1) in the form of a white powder, m.p. 98°–105° C.

In general accordance with the procedure of Example 2B, the compounds (104), (105), (106) and (108) (Table 1) are obtained starting from the HALS diols (208) |Example 2Ag|, (213) |Example 2Am|, (214) |Example 2An| and (216) |Example 2Ap| instead of from 2N-morpholino-4,6-bis|N-n-butyl-(N-2'-hydroxyethyl-2,2,6,6-tetramethylpiperidin-4-yl)amino|-1,3,5-triazine.

In general accordance with the procedure of Example 2B, compounds (107) is obtained (Table 1) starting from spirophosphorinane (301) |Inorganic Chemistry 31 (7), 1279–85 (1992)|

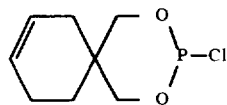
(301)

and the HALS diol (215) |Example 2Ao|.

In general accordance with the procedure of Example 2B and starting from the HALS diol (211) |Example 2Ak|, the compound (109) is obtained (Table 1).

TABLE 1

| No. | Compound | m.p. °C. | C (%), H (%), N (%), P(%) (calculated/found) | 31P-NMR (CDCl3) (ppm) |
|---|---|---|---|---|
| 101 | | oil | 54.18 9.88 3.01 13.30<br>54.13 9.37 3.04 13.16 | 124.04<br>124.32 |
| 102 | | oil | 54.32 9.12 5.51 12.18<br>53.66 9.06 5.41 12.14 | 124.55 |
| 103 | | 95-105 | 60.11 9.44 11.93 6.60<br>60.21 9.58 11.98 6.72 | 124.69 |
| 104 | | 52-62 | 60.18 9.54 10.92 6.90<br>56.69 9.45 10.59 6.95 | 122.34 |

TABLE 1-continued

| No. | Compound | m.p. °C. | C (%), H (%), N (%), P(%) (calculated/found) | 31P-NMR (CDCl3) (ppm) |
|---|---|---|---|---|
| 105 | | 150–167 | 51.99 7.85 7.28 10.73<br>52.09 7.98 7.36 10.51 | 122.40<br>123.38 |
| 106 | | 94–98 | 57.89 9.18 7.50 8.29<br>57.85 9.25 7.64 8.11 | 124.40 |
| 107 | | 130–135 | 59.89 8.33 2.18 9.65<br>59.92 8.35 2.33 9.54 | 124.28<br>125.48 |

TABLE 1-continued

| No. | Compound | m.p. °C. | C (%), H (%), N (%), P(%) (calculated/found) | ³¹P-NMR (CDCl₃) (ppm) |
|---|---|---|---|---|
| 108 | (structure) | 189–200 | 58.25 8.98 3.67 8.12<br>58.53 8.92 3.64 8.03 | 122.13 |
| 109 | (structure) | resin | 60.24 9.66 12.49 6.90<br>60.21 9.68 12.50 7.07 | 122.48 |

EXAMPLE 3

Stabilisation of multiple-extruded polypropylene 1.3 kg of polypropylene powder (Profax® 6501), which has been prestabilised with 0.025% of Irganox® 1076 (n-octadecyl (3-[3,5-di-tert-butyl-4-hydroxyphenyl] propionate] (melt flow index 3.2 measured at 230°/216 kg), are blended with 0.05% of Irganox® 1010 (pentaerythrityl tetrakis-[3(3,5di-tert-butyl-4-hydroxyphenyl)propionate), 0.05% of calcium stearate, 0.03% of dihydrotalcite [DHT 4A®, Kyowa Chemical Industry Co., Ltd., $Mg_{4.5}Al_2(OH)_{13}CO_3.3.5\ H_2O$] and 0.05% of the compound of Table 1. This blend is then extruded in an extruder having a cylinder diameter of 20 mm and a length of 400 mm at 100 rpm, the 3 heating zones being adjusted to the following temperatures: 260° C., 270° C. and 280° C. The extrudate is cooled by drawing it through a water bath and is then granulated. This granulate is repeatedly extruded. After 3 extrusions, the melt flow index is measured at 230° C./2.16 kg). A substantial increase in the melt index denotes pronounced chain degradation, i.e. poor stabilisation. The results are shown in Table 2.

TABLE 2

| Compound of Table 1 | melt flow index after 3 extrusions |
|---|---|
| — | 20.0 |
| 101 | 5.8 |
| 102 | 6.0 |
| 103 | 6.1 |
| 104 | 6.2 |
| 105 | 5.9 |
| 108 | 5.8 |
| 109 | 5.6 |

What is claimed is:

1. A compound of formula I

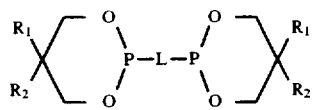
(I)

wherein L is a group of formula II or III $$-O-R_3-O-$$ (II)

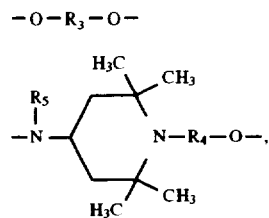
(III)

wherein $R_1$ and $R_2$ are each independently of the other hydrogen or $C_1-C_4$alkyl or, together with the linking carbon atom, are a 3,4-dehydrocyclohexylidene ring or 5-norbornenylidene ring.

$R_3$ is a group of formulae IV to XVI

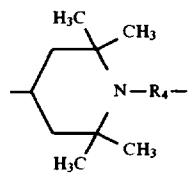
(IV)

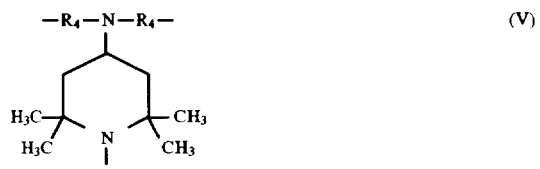
(V)

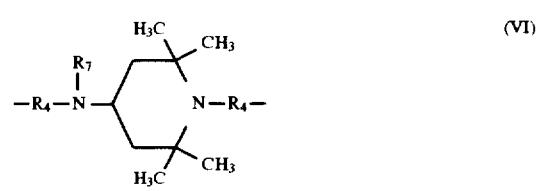
(VI)

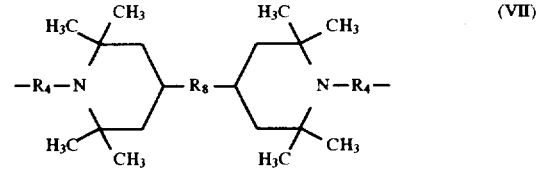
(VII)

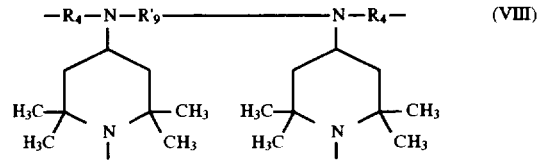
(VIII)

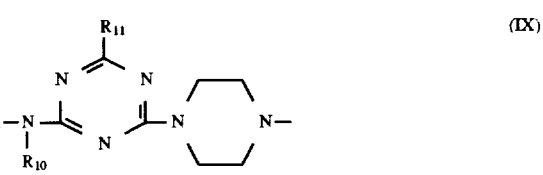
(IX)

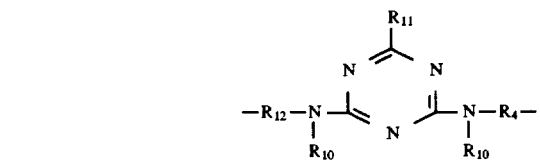
(X)

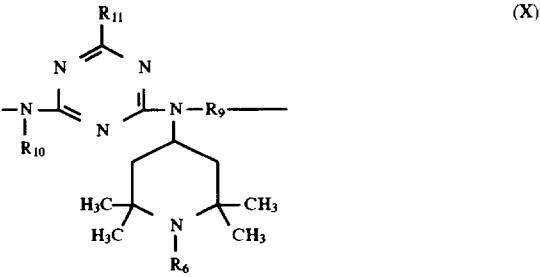

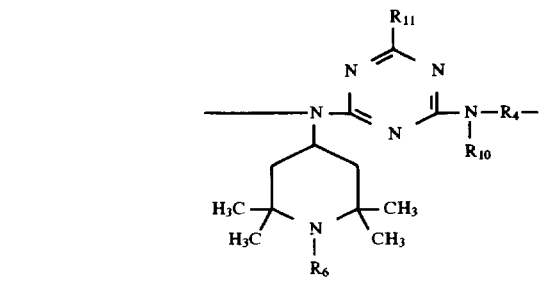

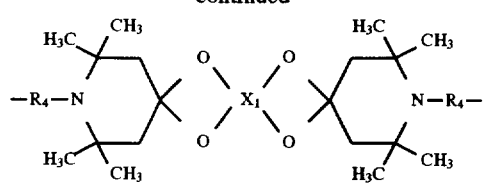  (XI)

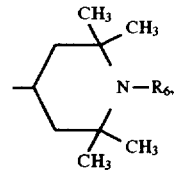  (XVII)

R$_5$ is C$_1$–C$_8$alkyl or a radical of formula XVII

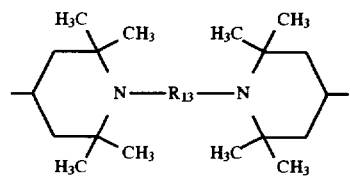  (XII)

R$_6$ is hydrogen, C$_1$–C$_8$alkyl, O$^{108}$, OH, NO, —CH$_2$CN, C$_1$–C$_{18}$alkoxy, C$_5$–C$_{12}$cycloalkoxy, C$_3$–C$_6$alkenyl, C$_3$–C$_6$alkynyl, C$_1$–C$_8$acyl, C$_7$–C$_9$ phenylalkyl which is unsubstituted or substituted at the phenyl ring by C$_1$–C$_4$alkyl;

R$_7$ is C$_1$–C$_8$alkyl or a radical of formula XVII

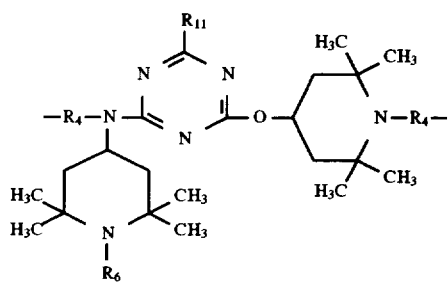  (XIII)

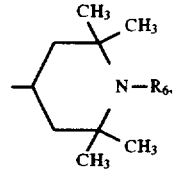  (XVII)

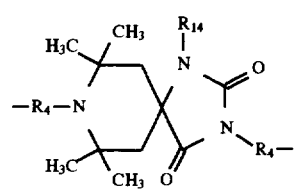  (XIV)

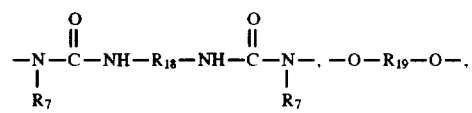

R$_8$ is 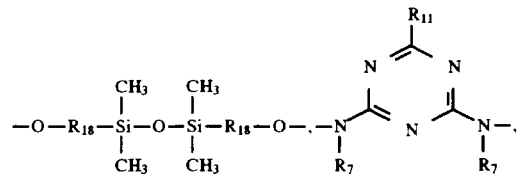

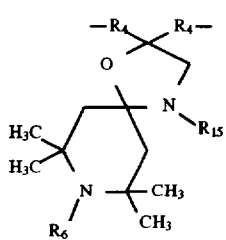  (XV)

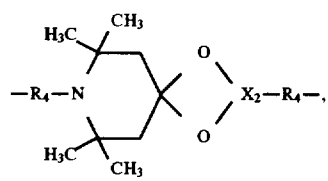  (XVI)

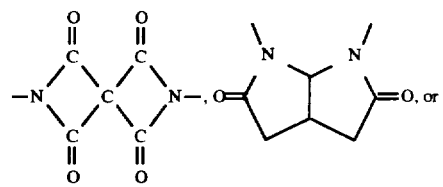

R$_4$ is C$_1$–C$_{18}$alkylene, C$_2$–C$_{18}$alkylene which is interrupted by oxygen, sulfur or

C$_4$–C$_8$ alkenylene or phenylethylene,

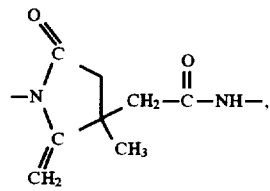

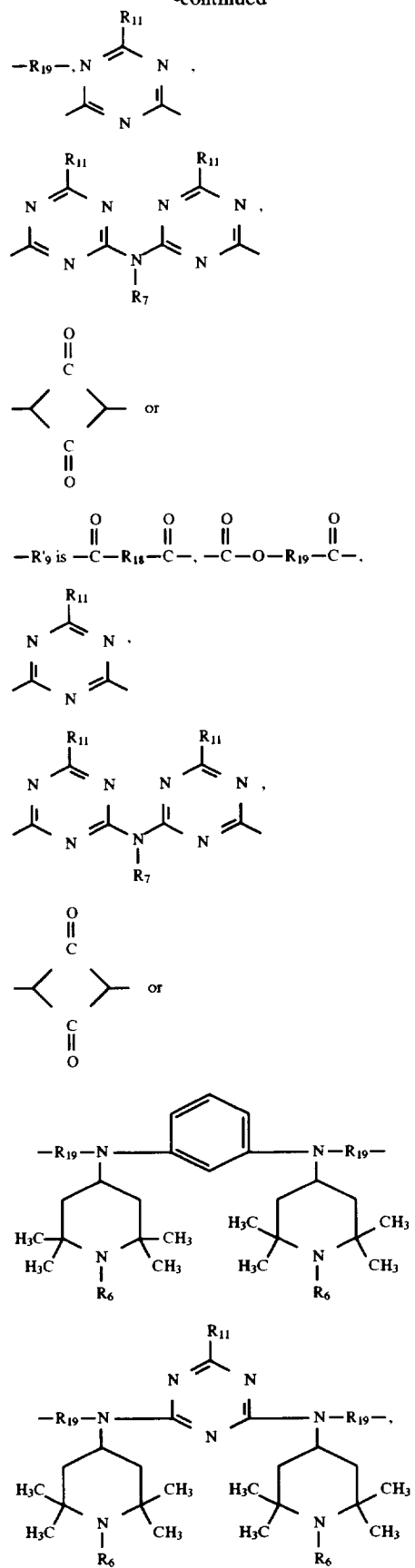
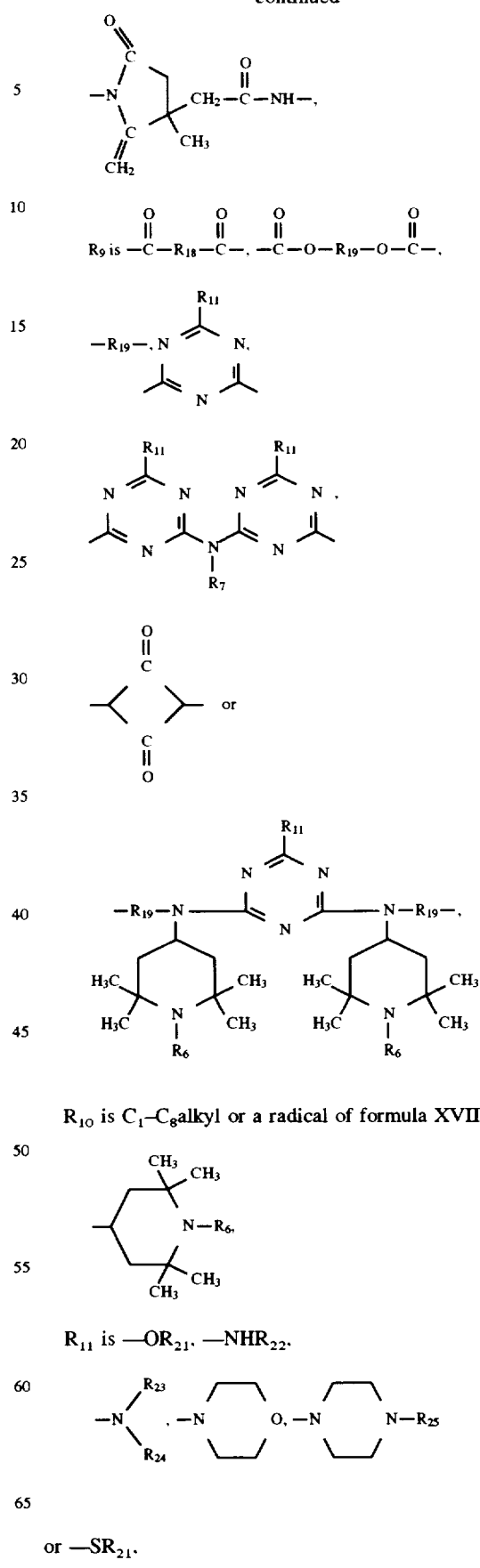
$R_{10}$ is $C_1$–$C_8$alkyl or a radical of formula XVII
$R_{11}$ is —$OR_{21}$, —$NHR_{22}$,
or —$SR_{21}$.

$R_{12}$ and $R_{13}$ are each independently of the other

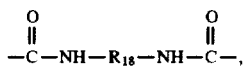

$C_1$–$C_{18}$alkylene, $C_2$–$C_{18}$alkylene which is interrupted by oxygen, sulfur or

$C_2$–$C_{18}$alkenylene, $C_2$–$C_{18}$alkynylene, $C_2$–$C_{20}$alkylidene, $C_7$–$C_{20}$phenylalkylidene, $C_5$–$C_8$cycloalkylene, $C_7$–$C_8$bicycloalkylene; phenylene or naphthylene which are unsubstituted or substituted by $C_1$–$C_4$alkyl;

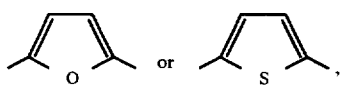

$R_{14}$ and $R_{15}$ are each independently of the other hydrogen or $C_1$–$C_8$alkyl, $R_{16}$ is hydrogen or $C_1$–$C_8$alkyl, $R_{17}$ is $C_1$–$C_8$alkyl, $R_{18}$ is a direct bond, $C_1$–$C_{18}$alkylene, $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, phenylene or naphthylene which are unsubstituted or substituted by $C_1$–$C_4$alkyl;

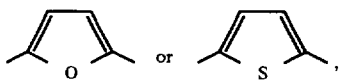

$R_{19}$ is $C_1$–$C_{18}$alkylene, $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, phenylene or naphthylene which are unsubstituted or substituted by $C_1$–$C_4$-alkyl;

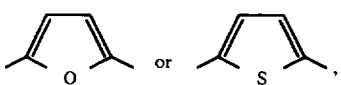

$R_{20}$ is $C_1$–$C_{25}$alkanoyl, benzoyl which is unsubstituted or substituted by $C_1$–$C_{12}$alkyl; or

$R_{21}$ is $C_1$–$C_{25}$alkyl, $C_2$–$C_{25}$alkyl which is interrupted by oxygen, sulfur or

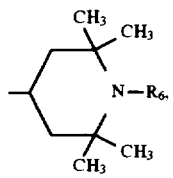

$C_2$–$C_{24}$alkenyl, $C_5$–$C_{15}$cycloalkyl which is unsubstituted or substituted by $C_1$–$C_4$alkyl; $C_5$–$C_{15}$cycloalkenyl which is unsubstituted or substituted by $C_1$–$C_4$alkyl; $C_7$–$C_9$phenylalkyl which is unsubstituted or substituted at the phenyl ring by $C_1$–$C_4$alkyl; phenyl which is unsubstituted or substituted by $C_1$–$C_4$alkyl;

$R_{22}$, $R_{23}$, $R_{24}$ and $R_{25}$ are each independently of one another hydrogen, $C_1$–$C_{18}$alkyl or a radical of formula XVII

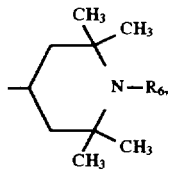  (XVII)

$R_{26}$ is $C_1$–$C_4$alkyl or hydroxymethyl, $R_{27}$ is hydrogen or $C_1$–$C_8$alkyl, $R_{28}$ is hydrogen, $C_1$–$C_8$alkyl or a radical of formula XVII

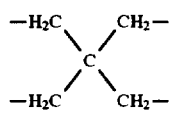  (XVII)

$R_{29}$ is hydrogen, $C_1$–$C_{20}$alkyl, $C_5$–$C_{12}$cycloalkyl, unsubstituted or $C_1$–$C_4$alkyl-substituted phenyl, $X_1$ is a group of formula XVIII, XIX, XX or XXI

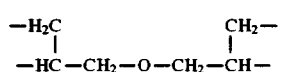  (XVIII)

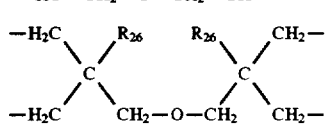  (XIX)

(XX)

-continued

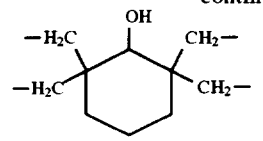

X₂ is —CH— or 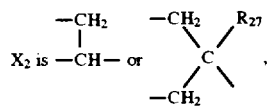,

X₃ is oxygen or 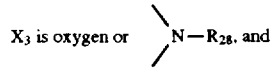, and

X₄ is 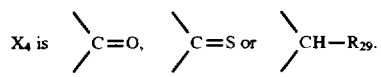.

2. A compound according to claim 1, wherein $R_4$ is $C_2$–$C_4$alkylene.

3. A compound according to claim 1, wherein $R_4$ is $C_1$–$C_{12}$alkylene, $C_4$–$C_8$alkylene which is interrupted by oxygen or sulfur; or $C_4$–$C_8$alkenylene, $R_5$ is $C_1$–$C_8$alkyl, $R_6$ is hydrogen, $C_1$–$C_8$alkyl, $O^{108}$, $C_4$–$C_{18}$alkoxy, $C_5$–$C_8$cycloalkoxy, $C_3$–$C_6$alkenyl, $C_3$–$C_6$alkynyl, $C_1$–$C_6$acyl or benzyl, $R_7$ is $C_1$–$C_8$alkyl, $R_8$ is 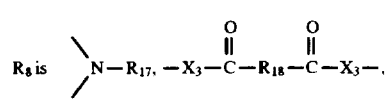,

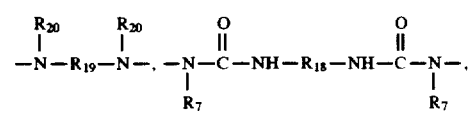,

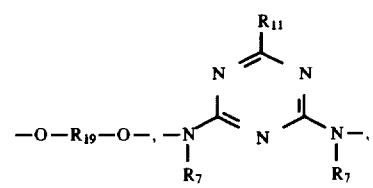, $R_9$ is 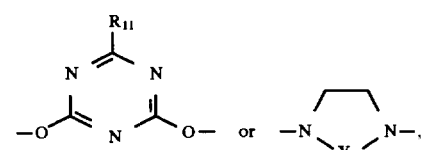,

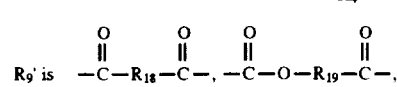,

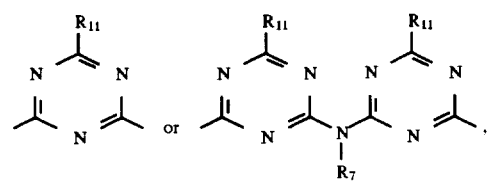, $R_{10}$ is $C_1$–$C_8$alkyl, $R_{11}$ is —$OR_{21}$, —$NHR_{22}$, (XXI)

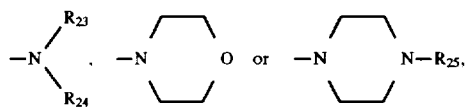, $R_{12}$ and $R_{13}$ are each independently of the other

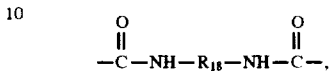, $C_1$–$C_{12}$alkylene, $C_4$–$C_{12}$alkylene which is interrupted by oxygen or sulfur; $C_2$–$C_{12}$alkenylene, $C_2$–$C_{12}$alkynylene, $C_2$–$C_{14}$alkylidene, $C_7$–$C_{16}$phenylalkylidene, $C_5$–$C_8$cycloalkylene, phenylene or naphthylene, $R_{14}$ and $R_{15}$ are each independently of the other hydrogen or $C_1$–$C_4$alkyl, $R_{18}$ is a direct bond, $C_1$–$C_{18}$alkylene, $C_4$–$C_{12}$alkylene which is interrupted by oxygen or sulfur; $C_2$–$C_{12}$alkenylene, $C_2$–$C_{14}$alkylidene, $C_7$–$C_{16}$phenylalkylidene, $C_5$–$C_8$cycloalkylene, phenylene or naphthylene, $R_{19}$ is $C_1$–$C_{12}$alkylene, $C_2$–$C_{12}$alkylene which is interrupted by oxygen or sulfur; $C_2$–$C_{12}$alkenylene, $C_2$–$C_{14}$alkylidene, $C_7$–$C_{16}$phenylalkylidene, $C_5$–$C_{18}$cycloalkylene, phenylene or naphthylene, $R_{20}$ is $C_1$–$C_{18}$alkanoyl, benzoyl or

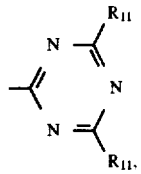, $R_{21}$ is $C_1$–$C_{18}$alkyl, $C_2$–$C_{18}$alkyl which is interrupted by oxygen or sulfur; $C_2$–$C_{18}$alkenyl, $C_5$–$C_8$cycloalkyl which is unsubstituted or substituted by $C_1$–$C_4$alkyl; $C_5$–$C_8$cycloalkenyl which is unsubstituted or substituted by $C_1$–$C_4$alkyl; $C_7$–$C_9$phenylalkyl, unsubstituted or $C_1$–$C_4$alkyl-substituted phenyl;

$R_{22}$, $R_{23}$, $R_{24}$ and $R_{25}$ are each independently of one another hydrogen or $C_1$–$C_{12}$alkyl, $R_{26}$ is $C_1$–$C_4$alkyl, $R_{27}$ is hydrogen or $C_1$–$C_4$alkyl, $R_{28}$ is hydrogen or $C_1$–$C_4$alkyl, $R_{29}$ is hydrogen, $C_1$–$C_{12}$alkyl, $C_5$–$C_8$cycloalkyl, unsubstituted or $C_1$–$C_4$alkyl-substituted phenyl, $X_1$ is a group of formula XVIII, XIX or XX

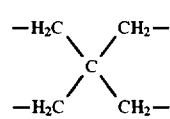 (XVIII)

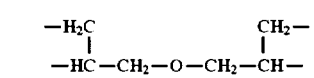 (XIX)
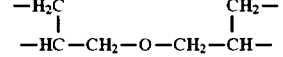

-continued

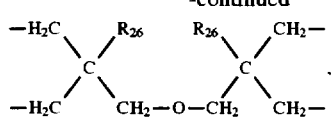  (XX)

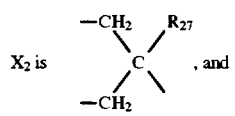

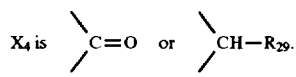

4. A compound according to claim 1, wherein $R_4$ is $C_2$–$C_8$alkylene, $C_4$–$C_{12}$alkylene which is interrupted by oxygen; or $C_4$–$C_8$alkenylene.

$R_5$ is $C_1$–$C_4$alkyl.

$R_6$ is hydrogen, $C_1$–$C_4$alkyl, $C_4$–$C_{18}$alkoxy, $C_5$–$C_8$cycloalkoxy, allyl, propargyl, acetyl or benzyl, $R_7$ is $C_1$–$C_8$alkyl.

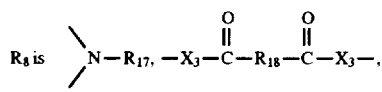

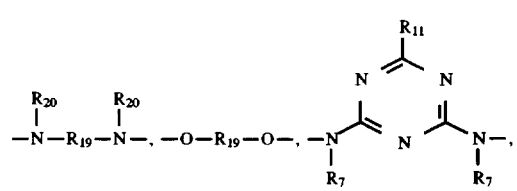

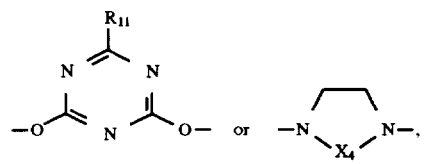

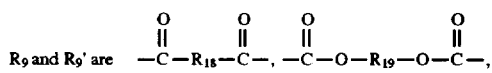

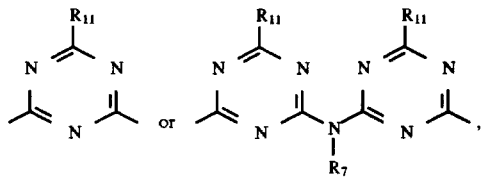

$R_{10}$ is $C_1$–$C_8$alkyl, $R_{11}$ is —$OR_{21}$, —$NHR_{22}$,

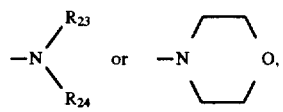

$R_{12}$ and $R_{13}$ are each independently of the other

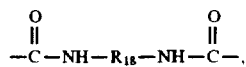

$C_1$–$C_8$alkylene, $C_4$–$C_{12}$-alkylene which is interrupted by oxygen; $C_2$–$C_8$alkenylene, $C_2$–$C_8$alkynylene, $C_2$–$C_{10}$alkylidene, $C_7$–$C_{12}$phenylalkylidene, cyclohexylene or phenylene, $R_{14}$ and $R_{15}$ are each independently of the other hydrogen or $C_1$–$C_4$alkyl, $R_{18}$ is a direct bond, $C_1$–$C_{12}$alkylene, $C_4$–$C_{12}$alkylene which is interrupted by oxygen; $C_2$–$C_8$alkenylene, $C_2$–$C_8$alkylidene, $C_7$–$C_{12}$phenylalkylidene, cyclohexylene or phenylene, $R_{19}$ is $C_1$–$C_{12}$alkylene, $C_2$–$C_{12}$alkylene which is interrupted by oxygen; $C_2$–$C_8$alkenylene, $C_2$–$C_8$alkylidene, $C_7$–$C_{12}$phenylalkylidene, cyclohexylene or phenylene, $R_{20}$ is $C_1$–$C_{12}$alkanoyl or benzoyl, $R_{21}$ is $C_1$–$C_{12}$alkyl, $C_2$–$C_{12}$alkyl which is interrupted by oxygen; $C_2$–$C_{12}$alkenyl, unsubstituted or $C_1$–$C_4$alkyl-substituted cyclohexyl; benzyl or phenyl, $R_{22}$, $R_{23}$ and $R_{24}$ are each independently of one another hydrogen or $C_1$–$C_8$alkyl, $R_{27}$ is hydrogen or $C_1$–$C_4$alkyl, $R_{28}$ is hydrogen or $C_1$–$C_4$alkyl, $R_{29}$ is hydrogen, $C_1$–$C_8$alkyl, cyclohexyl or phenyl, $X_1$ is a group of formula XVIII or XIX

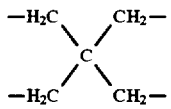  (XVIII)

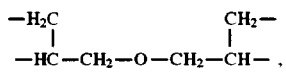  (XIX)

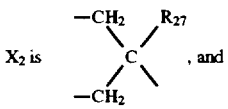

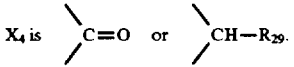

5. A compound according to claim 1, wherein

L is a group of formula II

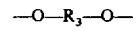  (II), $R_4$ is $C_2$–$C_8$alkylene, or $C_4$–$C_8$alkylene which is interrupted by oxygen, $R_5$ is $C_1$–$C_4$alkyl, $R_6$ is hydrogen, $C_1$–$C_4$alkyl, $C_4$–$C_{18}$alkoxy, $C_5$–$C_8$cycloalkoxy, allyl, propargyl, acetyl or benzyl, $R_7$ is $C_1$–$C_8$alkyl.

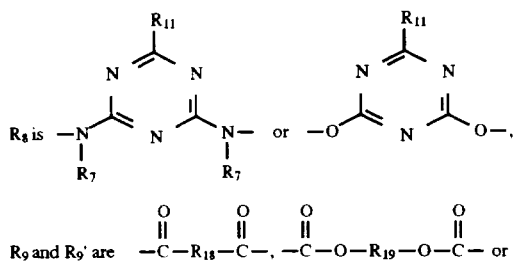

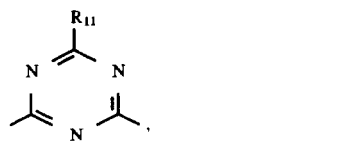

$R_{10}$ is $C_1$–$C_8$alkyl.
$R_{11}$ is —$OR_{21}$, —$NHR_{22}$,

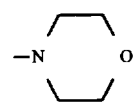

or —$SR_{21}$,
$R_{12}$ and $R_{13}$ are

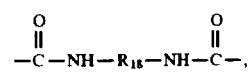

$R_{14}$ and $R_{15}$ are hydrogen.
$R_{18}$ is a direct bond, $C_1$–$C_8$alkylene, or $C_4$–$C_8$alkylene which is interrupted by oxygen.
$R_{19}$ is $C_2$–$C_8$alkylene, or $C_4$–$C_8$alkylene which is interrupted by oxygen.
$R_{21}$ is $C_1$–$C_8$alkyl, $C_4$–$C_{12}$alkyl which is interrupted by oxygen; or cyclohexyl.
$R_{22}$ is $C_1$–$C_8$alkyl.
$R_{27}$ is hydrogen or $C_1$–$C_4$alkyl.
$X_1$ is a group of formula XVIII or XIX

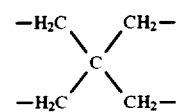 (XVIII)

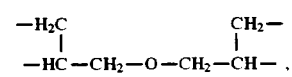 (XIX)

and $X_2$ is 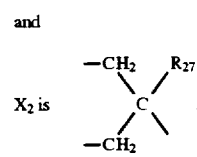

6. A compound according to claim 1, wherein
$R_6$ is hydrogen, $C_1$–$C_4$alkyl, $C_4$–$C_{16}$alkoxy, $C_5$–$C_8$cycloalkoxy, allyl, propargyl, acetyl or benzyl.
7. A compound according to claim 1, wherein
L is a group of formula II

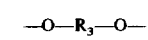 (II), $R_1$ and $R_2$ are methyl or, together with the linking carbon atom, form a 3,4-dehydrocyclohexylidene ring.

$R_3$ is a group of formula IV, V, VII, VIII, XI, XII, XIV or XVI

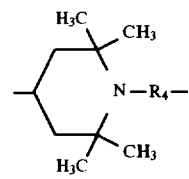 (IV)

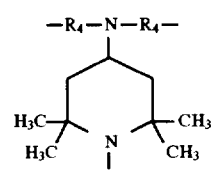 (V)

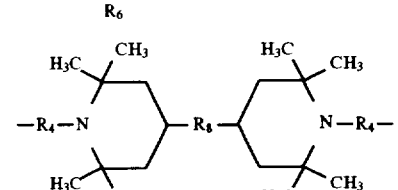 (VII)

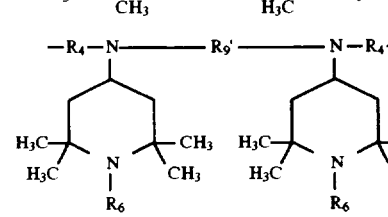 (VIII)

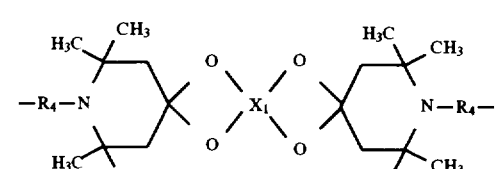 (XI)

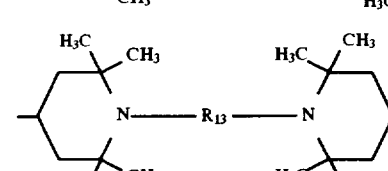 (XII)

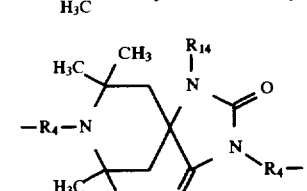 (XIV)

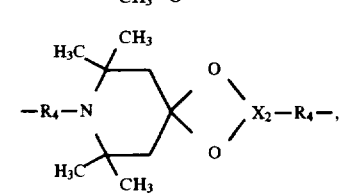 (XVI)

$R_4$ is ethylene.
$R_6$ is hydrogen or methyl.

R$_7$ is C$_1$–C$_6$alkyl,
R$_8$ is 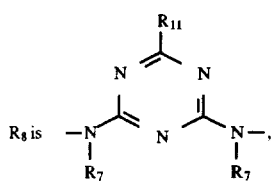,
R$_9'$ is 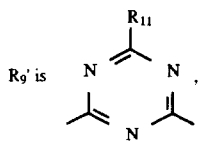,
R$_{11}$ is —OR$_{21}$, —HNR$_{22}$ or 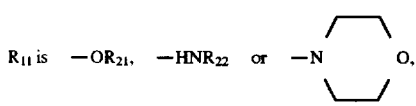,
R$_{13}$ is 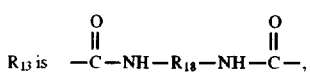,
R$_{14}$ is hydrogen,
R$_{18}$ is a direct bond or C$_1$–C$_8$alkylene,
R$_{21}$ is C$_1$–C$_4$alkyl,
R$_{22}$ is C$_1$–C$_8$alkyl,
R$_{27}$ is hydrogen or methyl.
X$_1$ is a group of formula XVIII
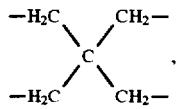 (XVIII)
and
X$_2$ is 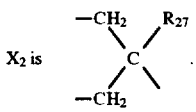.
* * * * *

UNITED STATES PATENT AND TRADEMARK OFFICE
CERTIFICATE OF CORRECTION

PATENT NO. : 5,777,113
DATED : JULY 7, 1998
INVENTOR(S) : RITA PITTELOUD

It is certified that error appears in the above-identified patent and that said Letters Patent is hereby corrected as shown below:

On the title page: Item

-- [30]     Foreign Application Priority Data

Oct. 12, 1994     [CH]     Switzerland..........................3066/94-3 --.

Signed and Sealed this

Fifth Day of January, 1999

Attest:

Attesting Officer

*Acting Commissioner of Patents and Trademarks*

UNITED STATES PATENT AND TRADEMARK OFFICE
CERTIFICATE OF CORRECTION

PATENT NO. : 5,777,113
DATED : July 7, 1998
INVENTOR(S) : Rita Pitteloud

It is certified that error appears in the above-identified patent and that said Letters Patent is hereby corrected as shown below:

Column 60, line 30, change "$R_q$" to --$R'_9$--.

Signed and Sealed this

Eleventh Day of May, 1999

Attest:

Q. TODD DICKINSON

*Attesting Officer*     *Acting Commissioner of Patents and Trademarks*